(12) United States Patent
Yip et al.

(10) Patent No.: US 7,181,349 B1
(45) Date of Patent: Feb. 20, 2007

(54) IDENTIFICATION OF COMPOUNDS FOR MODULATING DIMERIC RECEPTORS

(76) Inventors: Cecil Yip, 125 Melrose Avenue, Toronto (CA) M5M 1Y8; Peter Ottensmeyer, 27 Chatfield Drive, Don Mills, Ontario (CA) M3B 1K6; Robert Luo, 4020-H Blue Bonnet Blvd., Houston, TX (US) 77025

( * ) Notice: Subject to any disclaimer, the term of this patent is extended or adjusted under 35 U.S.C. 154(b) by 0 days.

(21) Appl. No.: 09/744,628

(22) PCT Filed: May 25, 2000

(86) PCT No.: PCT/CA00/00605

§ 371 (c)(1),
(2), (4) Date: Jun. 1, 2001

(87) PCT Pub. No.: WO00/73793

PCT Pub. Date: Dec. 7, 2000

Related U.S. Application Data

(63) Continuation-in-part of application No. 09/461,791, filed on Dec. 15, 1999, now abandoned.

(30) Foreign Application Priority Data

| May 27, 1999 | (CA) | ................................... | 2273576 |
| Dec. 16, 1999 | (CA) | ................................... | 2292258 |

(51) Int. Cl.
*G01N 31/00* (2006.01)
*G01N 33/48* (2006.01)
*G06F 19/00* (2006.01)

(52) U.S. Cl. .............................. 702/27; 702/19; 702/22

(58) Field of Classification Search .................. 702/19, 702/23, 150, 152, 153
See application file for complete search history.

(56) References Cited

U.S. PATENT DOCUMENTS

| 4,761,371 A | 8/1988 | Bell et al. |
| 5,646,242 A | 7/1997 | Baker et al. |
| 5,693,609 A | 12/1997 | Baker et al. |
| 5,700,662 A | 12/1997 | Chance et al. |

FOREIGN PATENT DOCUMENTS

| WO | WO 09/32017 | 7/1998 |
| WO | WO 99/28347 * | 6/1999 |

OTHER PUBLICATIONS

Lauri et al. (Journal of Computer-Aided Molecular Design (1994) vol. 8, pp. 51-66).*
Christiansen et al. (PNAS (1991) vol. 88, pp. 249-252).*
Luo, R., "Quaternary Structure of the Insulin-Insulin Receptor Complex", Science, 285:1077-1080 (1999).
McInnes, C., "Growth Factor Receptors: Structure, Mechanism, and Drug Discovery", Biopolymers 43(5):339-366 (1997) XP000972110.
Olsen, H., "The Relationship Between Insulin Bioactivity and Structure in the NH2-terminal A-chain Helix", *J. Mol. Biol.* 284:477-488 (1998) XP000965558.
F.P. Ottensmeyer, R. Z-T Luo, A.B. Fernandes, D. Beniac and C.C. Yip, "Insulin Receptor: 3D Reconstruction From Darkfield Stem Images, Structural Interpretation and Functional Model," Proceedings of the Microscopial Society of Canada, 26th Annual Meeting, May 26-28, 1999, University of Guelph, Guelph, Ontario, Canada.
F.P. Ottensmeyer, Daniel R. Beniac, Robert Z-T. Luo & Cecil C. Yip, "The Insulin Receptor: Structure, Ligand Binding and Mechanics of Transmembrane Signalling," Protein Engineering Network of Centres of Excellence Seminar, University of Toronto, Dec. 16, 1999, Toronto, Ontario, Canada.
F.P. Ottensmeyer, Daniel R. Beniac, Robert Z.-T. Luo and Cecil C. Yip, "Mechanism of Transmembrane Signaling: Insulin Binding and the Insulin Receptor," Biochemistry, vol. 39, No. 40, Oct. 10, 2000.
Lilli Petruzzelli, Roman Herrera and Ora M. Rosen, "Insulin receptor is an insulin-dependent tyrosine protein kinase: Copurification of insulin-binding activity and protein kinase activity to homogeneity from human placenta," Proc. Natl. Acad. Sci. USA, vol. 81, pp. 3327-3331, Jun. 1984, Biochemistry.
Melanie H. Cobb and Ora M. Rosen, "The Insulin Receptor and Tyrosine Protein Kinase Activity," Biochimica et Biophysica Acta, 738 (1984) 1-8.
A. Ullrich et al., "Human epidermal growth factor receptor cDNA sequence and aberrant expression of the amplified gene in A431 epidermoid carcinoma cells," Nature, vol. 309, pp. 418-425, May 1984.
J. Downward et al., "Close similarity of epidermal growth factor and v-erb-B oncogene protein sequences," Nature, vol. 307, pp. 521-527, Feb. 1984.
Todd W. Siegel et al., "Purification and Properties of the Human Placental Insulin Receptor," The Journal of Biological Chemistry, vol. 256, No. 17, Issue of Sep. 10, pp. 9266-9273, 1981.
George L. King et al., "Synthesis and Characterization of Molecular Hybrids of Insulin and Insulin-like Growth Factor I," The Journal of Biological Chemistry, vol. 257, No. 18, pp. 10869-10873, Sep. 1982.
C.C. Yip and P. Ottensmeyer. "Three-dimensional Structural Interactions of Insulin and its Receptor." J. Biol. Chem. 278:27329-27332, 2003.
C. Tan et al. "Structure-based de novo design of ligands using a three-dimensional model of the insulin receptor." Bioorganic & Medicinal Chemistry Letters, vol. 14: 1407-1410, 2004.
"Insulin-like growth factor I receptor precursor (CD221 antigen)", P08069. Created: Aug. 1, 1988, Sequence updated: Aug. 1, 1988. Annotation updated: Mar. 15, 2004.

* cited by examiner

*Primary Examiner*—Marjorie A. Moran
*Assistant Examiner*—Lori A. Clow
(74) *Attorney, Agent, or Firm*—McKee, Voorhees & Sease, P.L.C.

(57) ABSTRACT

The invention includes the fitted quaternary structure of insulin receptor. It also includes methods of identifying compounds that modulate insulin receptor activity by producing a compound that interacts with all or part of the fitted quaternary structure of insulin receptor or a fragment or derivative thereof and which thereby modulates insulin receptor activity.

11 Claims, 13 Drawing Sheets

(a)  Human Insulin

B-chain      FVNQH LCGSH LVEAL YLVCG ERGFF YTPKT

A-chain      GIVEQ CCTSI CSLYQ LENYC N (b)  Bovine Insulin    Bos taurus (Bovine)

B-chain      FVNQH LCGSH LVEAL YLVCG ERGFF YTPKA

A-chain      GIVEQ CCASV CSLYQ LENYC N (c)  Pig Insulin    Sus scrofa (Pig)

B-chain      FVNQH LCGSH LVEAL YLVCG ERGFF YTPKA

A-chain      GIVEQ CCTSI CSLYQ LENYC N

Figure 11

Human Insulin Receptor

Leader Sequence

MGTGGRRGAA AAPLLVAVAA LLLGAAG

Alpha subunit

| | | | | | |
|---|---|---|---|---|---|
| HLYPGEVCPG | MDIRNNLTRL | HELENCSVIE | GHLQILLMFK | TRPEDFRDLS | 50 |
| FPKLIMITDY | LLLFRVYGLE | SLKDLFPNLT | VIRGSRLFFN | YALVIFEMVH | 100 |
| LKELGLYNLM | NITRGSVRIE | KNNELCYLAT | IDWSRILDSV | EDNHIVLNKD | 150 |
| DNEECGDICP | GTAKGKTNCP | ATVINGQFVE | RCWTHSHCQK | VCPTICKSHG | 200 |
| CTAEGLCCHS | ECLGNCSQPD | DPTKCVACRN | FYLDGRCVET | CPPPYYHFQD | 250 |
| WRCVNFSFCQ | DLHHKCKNSR | RQGCHQYVIH | NNKCIPECPS | GYTMNSSNLL | 300 |
| CTPCLGPCPK | VCHLLEGEKT | IDSVTSAQEL | RGCTVINGSL | IINIRGGNNL | 350 |
| AAELEANLGL | IEEISGYLKI | RRSYALVSLS | FFRKLRLIRG | ETLEIGNYSF | 400 |
| YALDNQNLRQ | LWDWSKHNLT | TTQGKLFFHY | NPKLCLSEIH | KMEEVSGTKG | 450 |
| RQERNDIALK | TNGDKASCEN | ELLKFSYIRT | SFDKILLRWE | PYWPPDFRDL | 500 |
| LGFMLFYKEA | PYQNVTEFDG | QDACGSNSWT | VVDIDPPLRS | NDPKSQNHPG | 550 |
| WLMRGLKPWT | QYAIFVKTLV | TFSDERRTYG | AKSDIIYVQT | DATNPSVPLD | 600 |
| PISVSNSSSQ | IILKWKPPSD | PNGNITHYLV | FWERQAEDSE | LFELDYCLKG | 650 |
| LKLPSRTWSP | PFESEDSQKH | NQSEYEDSAG | ECCSCPKTDS | QILKELEESS | 700 |
| FRKTFEDYLH | NVVFVPRPS | | | | 719 |

Cutting site

| | | |
|---|---|---|
| | R KRR | 723 |

Beta subunit

| | | | | | |
|---|---|---|---|---|---|
| | | SLGDVGN | VTVAVPTVAA | FPNTSSTSVP | 750 |
| TSPEEHRPFE | KVVNKESLVI | SGLRHFTGYR | IELQACNQDT | PEERCSVAAY | 800 |
| VSARTMPEAK | ADDIVGPVTH | EIFENNVVHL | MWQEPKEPNG | LIVLYEVSYR | 850 |
| RYGDEELHLC | VSRKHFALER | GCRLRGLSPG | NYSVRIRATS | LAGNGSWTEP | 900 |
| TYFYVTDYLD | VPSNIAKIII | GPLIFVFLFS | VVIGSIYLFL | RKRQPDGPLG | 950 |
| PLYASSNPEY | LSASDVFPCS | VYVPDEWEVS | REKITLLREL | GQGSFGMVYE | 1000 |
| GNARDIIKGE | AETRVAVKTV | NESASLRERI | EFLNEASVMK | GFTCHHVVRL | 1050 |
| LGVVSKGQPT | LVVMELMAHG | DLKSYLRSLR | PEAENNPGRP | PPTLQEMIQM | 1100 |
| AAEIADGMAY | LNAKKFVHRD | LAARNCMVAH | DFTVKIGDFG | MTRDIYETDY | 1150 |
| YRKGGKGLLP | VRWMAPESLK | DGVFTTSSDM | WSFGVVLWEI | TSLAEQPYQG | 1200 |
| LSNEQVLKFV | MDGGYLDQPD | NCPERVTDLM | RMCWQFNPKM | RPTFLEIVNL | 1250 |
| LKDDLHPSFP | EVSFFHSEEN | KAPESEELEM | EFEDMENVPL | DRSSHCQREE | 1300 |
| AGGRDGGSSL | GFKRSYEEHI | PYTHMNGGKK | NGRILTLPRS | NPS | 1343 |

Fig. 12.

SEQUENCE LISTING

<160> NUMBER OF SEQ ID NOS: 17

<210> SEQ ID NO 1
<211> LENGTH: 30
<212> TYPE: PRT
<213> ORGANISM: Homo sapiens
<220> FEATURE:
<221> NAME/KEY: PEPTIDE

```
<222> LOCATION: (1)..(30)
<223> OTHER INFORMATION: X(1)=N,Q,T,Y  X(2)=K,R  X(3)=A,L,I,P,F,W,M,C,G
      X(4)=D  X(5)=Q,S,T,N  X(6)=A,V,I,P,F,W,M,C,G
      X(7)=D  X(8)=K,H  X(9)=A,V,I,P,L,W,M,C,G
      X(10)=A,V,I,P,L,W,M,C,G  X(11)=Q,S,T,N  X(12)=H,R

<400> SEQUENCE: 1

Phe Val Asn Gln His Leu Cys Gly Xaa Xaa Leu Xaa Xaa Ala Leu Xaa
1               5                   10                  15

Xaa Val Cys Gly Xaa Xaa Gly Xaa Xaa Xaa Thr Pro Xaa Thr
            20                  25                  30

<210> SEQ ID NO 2
<211> LENGTH: 21
<212> TYPE: PRT
<213> ORGANISM: Homo sapiens
<220> FEATURE:
<221> NAME/KEY: PEPTIDE
<222> LOCATION: (1)..(21)
<223> OTHER INFORMATION: X(1)=D  X(2)=Q,S,T,Y
      X(3)=N,Q,S,T,Y  X(4)=,Q,S,T,Y
      X(5)=D  X(6)=Q,S,T,Y

<400> SEQUENCE: 2

Gly Ile Val Xaa Xaa Cys Cys Xaa Ser Ile Cys Ser Leu Tyr Xaa Leu
1               5                   10                  15

Xaa Asn Tyr Cys Xaa
            20

<210> SEQ ID NO 3
<211> LENGTH: 30
<212> TYPE: PRT
<213> ORGANISM: Homo sapiens
<220> FEATURE:
<221> NAME/KEY: PEPTIDE
<222> LOCATION: (1)..(30)
<223> OTHER INFORMATION: X(1)=N,Q,T,Y  X(2)=K,R  X(3)=A,L,I,P,F,W,M,C,G
      X(4)=D  X(5)=Q,S,T,N  X(6)=A,V,I,P,F,W,M,C,G  X(7)=D  X(8)=K,H
      X(9)=A,V,I,P,L,W,M,C,G  X(10)=A,V,I,P,L,W,M,C,G  X(11)=Q,S,T,N
      X(13)=H,R

<400> SEQUENCE: 3

Phe Val Asn Gln His Leu Cys Gly Xaa Xaa Leu Xaa Xaa Ala Leu Xaa
1               5                   10                  15

Xaa Val Cys Gly Xaa Xaa Gly Xaa Xaa Xaa Thr Xaa Pro Thr
            20                  25                  30

<210> SEQ ID NO 4
<211> LENGTH: 21
<212> TYPE: PRT
<213> ORGANISM: Homo sapiens
<220> FEATURE:
<221> NAME/KEY: PEPTIDE
<222> LOCATION: (1)..(21)
<223> OTHER INFORMATION: X(1)=D  X(2)=Q,S,T,Y
      X(3)=N,Q,S,T,Y  X(4)=Q,S,T,Y
      X(5)=D  X(6)=Q,S,T,Y

<400> SEQUENCE: 4

Gly Ile Val Xaa Xaa Cys Cys Xaa Ser Ile Cys Ser Leu Tyr Xaa Leu
1               5                   10                  15

Xaa Asn Tyr Cys Xaa
            20

<210> SEQ ID NO 5
<211> LENGTH: 30
<212> TYPE: PRT
```

```
<213> ORGANISM: Bos taurus
<220> FEATURE:
<221> NAME/KEY: PEPTIDE
<222> LOCATION: (1)..(30)
<223> OTHER INFORMATION: X(1)=N,Q,T,Y  X(2)=K,R  X(3)=A,L,I,P,F,W,M,C,G
      X(4)=D  X(5)=Q,S,T,N  X(6)=A,V,I,P,F,W,M,C,G
      X(7)=D  X(8)=K,H  X(9)=A,V,I,P,L,W,M,C,G
      X(10)=A,V,I,P,L,W,M,C,G  X(11)=Q,S,T,N  X(12)=H,R

<400> SEQUENCE: 5

Phe Val Asn Gln His Leu Cys Gly Xaa Xaa Leu Xaa Xaa Ala Leu Xaa
1               5                   10                  15

Xaa Val Cys Gly Xaa Xaa Gly Xaa Xaa Xaa Thr Pro Xaa Ala
            20                  25                  30

<210> SEQ ID NO 6
<211> LENGTH: 21
<212> TYPE: PRT
<213> ORGANISM: Bos taurus
<220> FEATURE:
<221> NAME/KEY: PEPTIDE
<222> LOCATION: (1)..(21)
<223> OTHER INFORMATION: X(1)=D  X(2)=Q,S,T,Y
      X(3)=N,Q,S,T,Y  X(4)=Q,S,T,Y
      X(5)=D  X(6)=Q,S,T,Y

<400> SEQUENCE: 6

Gly Ile Val Xaa Xaa Cys Cys Xaa Ser Val Cys Ser Leu Tyr Xaa Leu
1               5                   10                  15

Xaa Asn Tyr Cys Xaa
            20

<210> SEQ ID NO 7
<211> LENGTH: 30
<212> TYPE: PRT
<213> ORGANISM: Sus scrofa
<220> FEATURE:
<221> NAME/KEY: PEPTIDE
<222> LOCATION: (1)..(30)
<223> OTHER INFORMATION: X(1)=N,Q,T,Y  X(2)=K,R  X(3)=A,L,I,P,F,W,M,C,G
      X(4)=D  X(5)=Q,S,T,N  X(6)=A,V,I,P,F,W,M,C,G
      X(7)=D  X(8)=K,H  X(9)=A,V,I,P,L,W,M,C,G
      X(10)=A,V,I,P,L,W,M,C,G  X(11)=Q,S,T,N  X(12)=H,R

<400> SEQUENCE: 7

Phe Val Asn Gln His Leu Cys Gly Xaa Xaa Leu Xaa Xaa Ala Leu Xaa
1               5                   10                  15

Xaa Val Cys Gly Xaa Xaa Gly Xaa Xaa Xaa Thr Pro Xaa Ala
            20                  25                  30

<210> SEQ ID NO 8
<211> LENGTH: 21
<212> TYPE: PRT
<213> ORGANISM: Sus scrofa
<220> FEATURE:
<221> NAME/KEY: PEPTIDE
<222> LOCATION: (1)..(21)
<223> OTHER INFORMATION: X(1)=D  X(2)=Q,S,T,Y
      X(3)=N,Q,S,T,Y  X(4)=Q,S,T,Y
      X(5)=D  X(6)=Q,S,T,Y

<400> SEQUENCE: 8

Gly Ile Val Xaa Xaa Cys Cys Xaa Ser Ile Cys Ser Leu Tyr Xaa Leu
1               5                   10                  15

Xaa Asn Tyr Cys Xaa
            20
```

-continued

<210> SEQ ID NO 9
<211> LENGTH: 30
<212> TYPE: PRT
<213> ORGANISM: Homo sapiens
<220> FEATURE:
<221> NAME/KEY: PEPTIDE
<222> LOCATION: (1)..(30)

<400> SEQUENCE: 9

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 10
<211> LENGTH: 21
<212> TYPE: PRT
<213> ORGANISM: Homo sapiens
<220> FEATURE:
<221> NAME/KEY: PEPTIDE
<222> LOCATION: (1)..(21)

<400> SEQUENCE: 10

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 11
<211> LENGTH: 30
<212> TYPE: PRT
<213> ORGANISM: Bos taurus
<220> FEATURE:
<221> NAME/KEY: PEPTIDE
<222> LOCATION: (1)..(30)

<400> SEQUENCE: 11

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala
            20                  25                  30

<210> SEQ ID NO 12
<211> LENGTH: 21
<212> TYPE: PRT
<213> ORGANISM: Bos taurus
<220> FEATURE:
<221> NAME/KEY: PEPTIDE
<222> LOCATION: (1)..(21)

<400> SEQUENCE: 12

Gly Ile Val Glu Gln Cys Cys Ala Ser Val Cys Ser Leu Tyr Gln Leu
1               5                   10                  15

Glu Asn Tyr Cys Asn
            20

<210> SEQ ID NO 13
<211> LENGTH: 30
<212> TYPE: PRT
<213> ORGANISM: Sus scrofa
<220> FEATURE:
<221> NAME/KEY: PEPTIDE
<222> LOCATION: (1)..(30)

<400> SEQUENCE: 13

Phe Val Asn Gln His Leu Cys Gly Ser His Leu Val Glu Ala Leu Tyr

```
                1               5                  10                 15
Leu Val Cys Gly Glu Arg Gly Phe Phe Tyr Thr Pro Lys Ala
                20                 25                 30

<210> SEQ ID NO 14
<211> LENGTH: 21
<212> TYPE: PRT
<213> ORGANISM: Sus scrofa
<220> FEATURE:
<221> NAME/KEY: PEPTIDE
<222> LOCATION: (1)..(21)

<400> SEQUENCE: 14

Gly Ile Val Glu Gln Cys Cys Thr Ser Ile Cys Ser Leu Tyr Gln Leu
1               5                  10                 15

Glu Asn Tyr Cys Asn
            20

<210> SEQ ID NO 15
<211> LENGTH: 27
<212> TYPE: PRT
<213> ORGANISM: Homo sapiens
<220> FEATURE:
<221> NAME/KEY: PEPTIDE
<222> LOCATION: (1)..(27)

<400> SEQUENCE: 15

Met Gly Thr Gly Gly Arg Arg Gly Ala Ala Ala Ala Pro Leu Leu Val
1               5                  10                 15

Ala Val Ala Ala Leu Leu Leu Gly Ala Ala Gly
            20                  25

<210> SEQ ID NO 16
<211> LENGTH: 719
<212> TYPE: PRT
<213> ORGANISM: Homo sapiens
<220> FEATURE:
<221> NAME/KEY: CHAIN
<222> LOCATION: (1)..(719)

<400> SEQUENCE: 16

His Leu Tyr Pro Gly Glu Val Cys Pro Gly Met Asp Ile Arg Asn Asn
1               5                  10                 15

Leu Thr Arg Leu His Glu Leu Glu Asn Cys Ser Val Ile Glu Gly His
            20                  25                 30

Leu Gln Ile Leu Leu Met Phe Lys Thr Arg Pro Glu Asp Phe Arg Asp
        35                  40                 45

Leu Ser Phe Pro Lys Leu Ile Met Ile Thr Asp Tyr Leu Leu Leu Phe
    50                  55                 60

Arg Val Tyr Gly Leu Glu Ser Leu Lys Asp Leu Phe Pro Asn Leu Thr
65              70                 75                  80

Val Ile Arg Gly Ser Arg Leu Phe Phe Asn Tyr Ala Leu Val Ile Phe
                85                 90                  95

Glu Met Val His Leu Lys Glu Leu Gly Leu Tyr Asn Leu Met Asn Ile
            100                 105                110

Thr Arg Gly Ser Val Arg Ile Glu Lys Asn Asn Glu Leu Cys Tyr Leu
        115                 120                125

Ala Thr Ile Asp Trp Ser Arg Ile Leu Asp Ser Val Glu Asp Asn His
    130                 135                140

Ile Val Leu Asn Lys Asp Asp Asn Glu Glu Cys Gly Asp Ile Cys Pro
145                 150                 155                160
```

-continued

```
Gly Thr Ala Lys Gly Lys Thr Asn Cys Pro Ala Thr Val Ile Asn Gly
            165                 170                 175
Gln Phe Val Glu Arg Cys Trp Thr His Ser His Cys Gln Lys Val Cys
        180                 185                 190
Pro Thr Ile Cys Lys Ser His Gly Cys Thr Ala Glu Gly Leu Cys Cys
    195                 200                 205
His Ser Glu Cys Leu Gly Asn Cys Ser Gln Pro Asp Asp Pro Thr Lys
210                 215                 220
Cys Val Ala Cys Arg Asn Phe Tyr Leu Asp Gly Arg Cys Val Glu Thr
225                 230                 235                 240
Cys Pro Pro Pro Tyr Tyr His Phe Gln Asp Trp Arg Cys Val Asn Phe
                245                 250                 255
Ser Phe Cys Gln Asp Leu His His Lys Cys Lys Asn Ser Arg Arg Gln
            260                 265                 270
Gly Cys His Gln Tyr Val Ile His Asn Asn Lys Cys Ile Pro Glu Cys
        275                 280                 285
Pro Ser Gly Tyr Thr Met Asn Ser Ser Asn Leu Leu Cys Thr Pro Cys
    290                 295                 300
Leu Gly Pro Cys Pro Lys Val Cys His Leu Leu Glu Gly Glu Lys Thr
305                 310                 315                 320
Ile Asp Ser Val Thr Ser Ala Gln Glu Leu Arg Gly Cys Thr Val Ile
                325                 330                 335
Asn Gly Ser Leu Ile Ile Asn Ile Arg Gly Gly Asn Asn Leu Ala Ala
            340                 345                 350
Glu Leu Glu Ala Asn Leu Gly Leu Ile Glu Glu Ile Ser Gly Tyr Leu
        355                 360                 365
Lys Ile Arg Arg Ser Tyr Ala Leu Val Ser Leu Ser Phe Phe Arg Lys
    370                 375                 380
Leu Arg Leu Ile Arg Gly Glu Thr Leu Glu Ile Gly Asn Tyr Ser Phe
385                 390                 395                 400
Tyr Ala Leu Asp Asn Gln Asn Leu Arg Gln Leu Trp Asp Trp Ser Lys
                405                 410                 415
His Asn Leu Thr Thr Thr Gln Gly Lys Leu Phe Phe His Tyr Asn Pro
            420                 425                 430
Lys Leu Cys Leu Ser Glu Ile His Lys Met Glu Glu Val Ser Gly Thr
        435                 440                 445
Lys Gly Arg Gln Glu Arg Asn Asp Ile Ala Leu Lys Thr Asn Gly Asp
    450                 455                 460
Lys Ala Ser Cys Glu Asn Glu Leu Leu Lys Phe Ser Tyr Ile Arg Thr
465                 470                 475                 480
Ser Phe Asp Lys Ile Leu Leu Arg Trp Glu Pro Tyr Trp Pro Pro Asp
                485                 490                 495
Phe Arg Asp Leu Leu Gly Phe Met Leu Phe Tyr Lys Glu Ala Pro Tyr
            500                 505                 510
Gln Asn Val Thr Glu Phe Asp Gly Gln Asp Ala Cys Gly Ser Asn Ser
        515                 520                 525
Trp Thr Val Val Asp Ile Asp Pro Pro Leu Arg Ser Asn Asp Pro Lys
    530                 535                 540
Ser Gln Asn His Pro Gly Trp Leu Met Arg Gly Leu Lys Pro Trp Thr
545                 550                 555                 560
Gln Tyr Ala Ile Phe Val Lys Thr Leu Val Thr Phe Ser Asp Glu Arg
                565                 570                 575
```

```
Arg Thr Tyr Gly Ala Lys Ser Asp Ile Ile Tyr Val Gln Thr Asp Ala
            580                 585                 590

Thr Asn Pro Ser Val Pro Leu Asp Pro Ile Ser Val Ser Asn Ser Ser
        595                 600                 605

Ser Gln Ile Ile Leu Lys Trp Lys Pro Ser Asp Pro Asn Gly Asn
    610                 615                 620

Ile Thr His Tyr Leu Val Phe Trp Glu Arg Gln Ala Glu Asp Ser Glu
625                 630                 635                 640

Leu Phe Glu Leu Asp Tyr Cys Leu Lys Gly Leu Lys Leu Pro Ser Arg
                645                 650                 655

Thr Trp Ser Pro Pro Phe Glu Ser Glu Asp Ser Gln Lys His Asn Gln
            660                 665                 670

Ser Glu Tyr Glu Asp Ser Ala Gly Glu Cys Cys Ser Cys Pro Lys Thr
        675                 680                 685

Asp Ser Gln Ile Leu Lys Glu Leu Glu Ser Ser Phe Arg Lys Thr
    690                 695                 700

Phe Glu Asp Tyr Leu His Asn Val Val Phe Val Pro Arg Pro Ser
705                 710                 715

<210> SEQ ID NO 17
<211> LENGTH: 620
<212> TYPE: PRT
<213> ORGANISM: Homo sapiens
<220> FEATURE:
<221> NAME/KEY: CHAIN
<222> LOCATION: (1)..(620)

<400> SEQUENCE: 17

Ser Leu Gly Asp Val Gly Asn Val Thr Val Ala Val Pro Thr Val Ala
1               5                   10                  15

Ala Phe Pro Asn Thr Ser Ser Thr Ser Val Pro Thr Ser Pro Glu Glu
                20                  25                  30

His Arg Pro Phe Glu Lys Val Val Asn Lys Glu Ser Leu Val Ile Ser
            35                  40                  45

Gly Leu Arg His Phe Thr Gly Tyr Arg Ile Glu Leu Gln Ala Cys Asn
        50                  55                  60

Gln Asp Thr Pro Glu Glu Arg Cys Ser Val Ala Ala Tyr Val Ser Ala
65                  70                  75                  80

Arg Thr Met Pro Glu Ala Lys Ala Asp Asp Ile Val Gly Pro Val Thr
                85                  90                  95

His Glu Ile Phe Glu Asn Asn Val His Leu Met Trp Gln Glu Pro
            100                 105                 110

Lys Glu Pro Asn Gly Leu Ile Val Leu Tyr Glu Val Ser Tyr Arg Arg
        115                 120                 125

Tyr Gly Asp Glu Glu Leu His Leu Cys Val Ser Arg Lys His Phe Ala
    130                 135                 140

Leu Glu Arg Gly Cys Arg Leu Arg Gly Leu Ser Pro Gly Asn Tyr Ser
145                 150                 155                 160

Val Arg Ile Arg Ala Thr Ser Leu Ala Gly Asn Gly Ser Trp Thr Glu
                165                 170                 175

Pro Thr Tyr Phe Tyr Val Thr Asp Tyr Leu Asp Val Pro Ser Asn Ile
            180                 185                 190

Ala Lys Ile Ile Ile Gly Pro Leu Ile Phe Val Phe Leu Phe Ser Val
        195                 200                 205

Val Ile Gly Ser Ile Tyr Leu Phe Leu Arg Lys Arg Gln Pro Asp Gly
    210                 215                 220
```

-continued

```
Pro Leu Gly Pro Leu Tyr Ala Ser Ser Asn Pro Glu Tyr Leu Ser Ala
225                 230                 235                 240

Ser Asp Val Phe Pro Cys Ser Val Tyr Val Pro Asp Glu Trp Glu Val
            245                 250                 255

Ser Arg Glu Lys Ile Thr Leu Leu Arg Glu Leu Gly Gln Gly Ser Phe
            260                 265                 270

Gly Met Val Tyr Glu Gly Asn Ala Arg Asp Ile Ile Lys Gly Glu Ala
            275                 280                 285

Glu Thr Arg Val Ala Val Lys Thr Val Asn Glu Ser Ala Ser Leu Arg
290                 295                 300

Glu Arg Ile Glu Phe Leu Asn Glu Ala Ser Val Met Lys Gly Phe Thr
305                 310                 315                 320

Cys His His Val Val Arg Leu Leu Gly Val Val Ser Lys Gly Gln Pro
                325                 330                 335

Thr Leu Val Val Met Glu Leu Met Ala His Gly Asp Leu Lys Ser Tyr
                340                 345                 350

Leu Arg Ser Leu Arg Pro Glu Ala Glu Asn Asn Pro Gly Arg Pro Pro
            355                 360                 365

Pro Thr Leu Gln Glu Met Ile Gln Met Ala Ala Glu Ile Ala Asp Gly
370                 375                 380

Met Ala Tyr Leu Asn Ala Lys Lys Phe Val His Arg Asp Leu Ala Ala
385                 390                 395                 400

Arg Asn Cys Met Val Ala His Asp Phe Thr Val Lys Ile Gly Asp Phe
                405                 410                 415

Gly Met Thr Arg Asp Ile Tyr Glu Thr Asp Tyr Tyr Arg Lys Gly Gly
                420                 425                 430

Lys Gly Leu Leu Pro Val Arg Trp Met Ala Pro Glu Ser Leu Lys Asp
            435                 440                 445

Gly Val Phe Thr Thr Ser Ser Asp Met Trp Ser Phe Gly Val Val Leu
450                 455                 460

Trp Glu Ile Thr Ser Leu Ala Glu Gln Pro Tyr Gln Gly Leu Ser Asn
465                 470                 475                 480

Glu Gln Val Leu Lys Phe Val Met Asp Gly Gly Tyr Leu Asp Gln Pro
                485                 490                 495

Asp Asn Cys Pro Glu Arg Val Thr Asp Leu Met Arg Met Cys Trp Gln
            500                 505                 510

Phe Asn Pro Lys Met Arg Pro Thr Phe Leu Glu Ile Val Asn Leu Leu
            515                 520                 525

Lys Asp Asp Leu His Pro Ser Phe Pro Glu Val Ser Phe Phe His Ser
530                 535                 540

Glu Glu Asn Lys Ala Pro Glu Ser Glu Glu Leu Glu Met Glu Phe Glu
545                 550                 555                 560

Asp Met Glu Asn Val Pro Leu Asp Arg Ser Ser His Cys Gln Arg Glu
                565                 570                 575

Glu Ala Gly Gly Arg Asp Gly Gly Ser Ser Leu Gly Phe Lys Arg Ser
            580                 585                 590

Tyr Glu Glu His Ile Pro Tyr Thr His Met Asn Gly Gly Lys Lys Asn
            595                 600                 605

Gly Arg Ile Leu Thr Leu Pro Arg Ser Asn Pro Ser
610                 615                 620
```

IDENTIFICATION OF COMPOUNDS FOR MODULATING DIMERIC RECEPTORS

This application is a continuation-in-part of U.S. Ser. No. 09/461,791 filed Dec. 15, 1999, now abandoned.

FIELD OF THE INVENTION

The invention relates to methods of using the three dimensional structure of an intrinsically covalent dimeric receptor, preferably the insulin receptor, to identify test compounds that will interact with the dimeric receptor and modulate its activity. The invention also includes compounds identified using the methods of the invention.

BACKGROUND OF THE INVENTION

Covalent dimeric receptors are found on almost all cells in mammals. These receptors include IR (insulin receptor), IGF-I R (insulin-like growth factor I) and IRR (the insulin receptor-related receptor). In the case of IR, insulin binding to IR is essential for its manifold effects such as glucose homeostasis, increased protein synthesis, growth, and development in mammals. IR belongs to the superfamily of transmembrane receptor TKs that include the monomeric epidermal growth factor receptor (EGFR) and platelet-derived growth factor receptor (PDGFR). In contrast, IR and its homologues IGF-I R and IRR are sub-types of this family that are intrinsic disulfide-linked dimers of two heterodimers of the form $(\alpha\beta)_2$ (1,2). Monomeric receptor TKs are inactive, but are activated by ligand-induced dimerization that results in autophosphorylation. Dimeric IR-like TKs are also inactive, and are activated by ligand binding without further dimerization. Insulin binding to the extracellular domain of IR results in autophosphorylation of specific tyrosines in the cytoplasmic domain to initiate an intracellular signal transduction cascade (3). However, the structural basis for the mechanism of IR activation by extracellular insulin binding has not been elucidated because the quaternary structure of IR was unknown. Only some of the smaller domains have yielded high resolution structural information.

Diabetes may be caused by mutant IR (eg. acanthosis nigrican or leprechaunism. Insulin resistance leading to diabetes or similar symptoms may also occur.). Diseases are also caused by insufficient amounts of IR ligand. For example, in diabetes, the pancreas produces insufficient amounts of insulin. Insulin activates IR and allows cells to absorb and store glucose. In the absence of adequate insulin, glucose accumulates in excessive amounts in the blood (hyperglycemia). The symptoms of diabetes may include poor blood circulation, blindness and organ damage. These symptoms often lead to premature death.

Diabetes is presently treated by insulin replacement therapy. This treatment has been very successful, but it still has problems such as glycemic control. Poor glycemic control can cause retinopathy, poor blood circulation and the other problems associated with diabetes. It is also difficult to formulate insulin for slow release. Modified insulins have been created in an attempt to address problems with insulin therapy. In some cases, "super-insulins" have been created to increase the activation of insulin receptor by its ligand. In other cases, binding to insulin receptor is not substantially increased, but the ligand has more favourable formulation properties. For example, in Humalog™ (SEQ ID NO:3 and SEQ ID NO:4), a lysine and a proline in insulin are switched to provide more favourable solubility characteristics.

These drug design strategies have been based on limited information, such as the chemical properties of the insulin molecule. In some cases, insulin has been randomly modified and then assayed to determine the effects on insulin activity. While there has been success in producing insulin variants, both of these approaches are time consuming because variants are made without a clear understanding of the effect of the variation on binding to insulin receptor. There is a need to obtain additional information about the insulin receptor in order to provide a rational basis for drug design.

For example, it would be helpful if the quaternary structure, including the ligand binding site, of IR was available and characterized to the detail of amino acids. However, it is very difficult to obtain information about the quaternary structure of dimeric receptors. For example, large transmembrane proteins such as cell surface hormone receptors have been difficult to crystallize as intact molecules for high-resolution structural study. They are also too large for NMR spectroscopy. The 480-kDa insulin receptor (IR) has thus not been crystallized as an intact molecule, and its quaternary structure remains unknown to date.

SUMMARY OF THE INVENTION

We have obtained the quaternary structure of IR. We used low-dose low-temperature dark field scanning transmission electron microscopy (STEM). Using electron micrographs of the insulin-IR complex we have reconstructed the three-dimensional quaternary structure of the intact receptor complexed with gold-labeled insulin ligand. Although IR has been purified and studied for over 15 years, this is the first 3D reconstruction of its entire dimeric structure. Contiguous high densities within the 3D structure indicate a two-fold symmetry for this dimeric membrane receptor, as well as a logical sequence for its biochemical subdomains from the observed binding of a single insulin on the ectodomain to the juxtaposition of the pair of intrinsic tyrosine kinases (TKs) of the intracellular domain.

We determined structural relationships of the IR subdomains in the 3D reconstruction of IR and a structural basis for IR activation by insulin. In the absence of ATP which is required to complete the activation of the IR tyrosine kinase, the structure of this insulin-bound IR can be considered to be in a transitional state, with its kinase domains intermediate between the inactive and activated structures observed by x-ray crystallography (4).

The quaternary structure of IR, fitted with the atomic co-ordinates of highly analogous domains of IR has resulted in a detailed description of the insulin binding site on the insulin receptor. Moreover, the combination of structural detail from 20 Å to atomic resolution yielded a self-consistent model for the mechanism of the initial phase of insulin action on binding to effect intracellular receptor tyrosine kinase activation.

The complete IR model provides a simple mechanical paradigm for the reversible transmembrane signalling response. It explains the need for the complexity of structural components to control both inhibition and accommodation of tyrosine kinase activation. It gives ready structural explanations for many normal effects, for various mutations and for mild chemical reduction of the insulin receptor. It thus provides a comprehensive structural basis for the mechanics of transmembrane signal transduction for the intrinsically dimeric insulin-like membrane receptors.

The details of the insulin binding site provide an explanation of binding of normal human insulin (including recombinantly produced insulin such as Novolin™) as well as of the lesser or greater binding of insulin from other animals to the human IR (SEQ ID NO:15, SEQ ID NO:16 and SEQ ID NO:17) and explains the binding of modified insulins such as "super-insulins", Humalog™ (SEQ ID NO:3 and SEQ ID NO:4) and other insulin analogs.

One aspect of the invention includes a method of identifying a compound that modulates insulin receptor activity, including producing a compound that interacts with all or part of the fitted quaternary structure of insulin receptor or a fragment or derivative thereof and which thereby modulates insulin receptor activity. In one embodiment, the method further includes synthesizing the compounds. The method preferably involves producing the compound based on its interaction with the fitted quaternary structure of insulin receptor or a fragment or derivative thereof. For example, one may produce the compound based on mimicking all or part of the IR:insulin amino acid interactions.

Another aspect of the invention includes a method of identifying a compound that modulates insulin receptor activity, including comparing the structure of a compound for modulating insulin receptor activity to all or part of the fitted quaternary structure of insulin receptor or a fragment or derivative thereof to determine whether the compound is likely to modulate insulin receptor activity.

The method may further include determining whether the compound modulates the activity of the insulin receptor or a fragment or a derivative thereof having IR activity in an in vivo or in vitro assay. The compound identified by the method is an IR agonist or an IR antagonist. In one variation, the fitted quaternary structure of IR comprises substantially the entire fitted quaternary structure of IR.

The method may further include:
a) introducing into a computer program information defining a ligand binding site conformation including at least one residue from monomer A in Table I and at least one residue from monomer B in Table I, the ligand binding site defined by the approximate amino acid distances listed in Table I, wherein the program displays the quaternary structure thereof, fitted with the atomic coordinates of the subdomains;
b) comparing the structural coordinates of the compound to the structural coordinates of the ligand binding site and determining whether the compound fits spatially into the ligand binding site and is capable of changing IR from an inactive conformation to an active conformation or biasing IR toward an active conformation;
wherein the ability to change IR from an inactive conformation to an active conformation or bias IR toward an active conformation is predictive of the ability of the compound to agonize IR activity.

The method may further include preparing the compound that fits spatially into the ligand binding site and determining whether the compound agonizes IR activity in an IR activity assay. The invention also includes a method of identifying a compound which agonizes IR or a fragment or derivative thereof having IR activity, the IR, fragment or derivative including a ligand binding site with at least one of the residues and approximate structural coordinates of each of monomer A and monomer B listed in Table 1, the method including the steps of:
a) providing the coordinates of the ligand binding site of the IR to a computerized modeling system;
b) identifying compounds which interact with the ligand binding site and change IR from an inactive conformation to an active conformation or bias IR toward an active conformation.

The invention also includes a method of drug design including using at least one of the amino acids of each of monomer A and monomer B of IR in Table I to determine whether a compound interacts with the ligand binding site of IR or a fragment or derivative thereof having IR activity and is capable of changing IR from an inactive conformation to an active conformation or biasing IR toward an active conformation.

Another aspect of the invention includes a method of agonizing IR including administering to a mammal a compound that fits spatially into the ligand binding site of IR, the compound interacting with at least
  a) one IR amino acid in monomer A listed in Table 1; and
  b) one IR amino acid in monomer B listed in Table 1;
  wherein the compound is capable of changing IR from an inactive conformation to an active conformation or biasing IR toward an active conformation.

The method may further include:
a) introducing into a computer program information defining a ligand binding site conformation including at least one residue from monomer A in Table I and at least one residue from monomer B in Table I, the ligand binding site defined by the approximate amino acid coordinates listed in Table I, wherein the program displays the quaternary structure thereof;
b) comparing the structural coordinates of the compound to the structural coordinates of the ligand binding site and determining whether the compound fits spatially into the ligand binding site and is capable of changing IR from an active conformation to an inactive conformation or biasing IR toward an inactive conformation;
wherein the ability to change IR from an active conformation to an inactive conformation or bias IR toward an inactive conformation is predictive of the ability of the compound to antagonize IR activity.

The method may include preparing the compound that fits spatially into the ligand binding site and determining whether the test compound antagonizes IR activity in an IR activity assay.

Another aspect of the invention includes a method of identifying a compound which antagonizes IR or a fragment or derivative thereof having IR activity, the IR, fragment or derivative including a ligand binding site with at least one of the residues and approximate distances of each of monomer A and monomer B listed in Table I, the method including the steps of:
a) providing the coordinates of the ligand binding site of the IR to a computerized modeling system;
b) identifying compounds which interact with the ligand binding site and change IR from an active conformation to an inactive conformation or bias IR toward an inactive conformation.

A variation of the invention includes a method of drug design including using at least one of the structural coordinates from each of monomer A and monomer B of IR in Table 1 to determine whether a compound interacts with the ligand binding site of IR or a fragment or derivative thereof having IR activity and is capable of changing IR from an active conformation to an inactive conformation or biasing IR toward an inactive conformation.

The invention also includes a method of antagonizing IR by administering to a mammal a compound that fits spatially into the ligand binding site of IR, the compound interacting with at least:
a) one IR amino acid in monomer A listed in Table 1; and
b) one IR amino acid in monomer B listed in Table 1;

wherein the compound is capable of changing IR from an active conformation to an inactive conformation or biasing IR toward an active conformation. In a variation of the method, the ability of the compound to fit spatially into the ligand binding site is determined by comparing the structural coordinates of the compound with the structural coordinates of IR. The ability of the compound to change the conformation of IR can be determined by comparing the structural coordinates of the compound with the structural coordinates of IR.

Another variation of the invention includes:
a) introducing into a computer program information defining a cam including at least one residue from the Cam-loop segment in Table 2 and at least one residue from the L1 surface in Table 2, wherein the program displays the structure thereof and its relation to other IR domains;
b) comparing the structural coordinates of the compound to the structural coordinates of the cam and determining whether the compound interacts with the cam and is capable of changing IR from an inactive conformation to an active conformation or biasing IR toward an active conformation;

wherein the ability to change IR from an inactive conformation to an active conformation is predictive of the ability of the compound to agonize IR activity. The method can further include preparing the compound that interacts with the cam and determining whether the test compound agonizes IR activity in an IR activity assay. The invention includes a method of identifying a compound which agonizes IR or a fragment or derivative thereof having IR activity, the IR, fragment or derivative including a cam with at least one of the residues and approximate structural coordinates of the cam-loop segment and the L1 surface listed in Table 2, the method including the steps of:
a) providing the coordinates of the cam to a computerized modeling system;
b) determining compounds which interact with the cam and change IR from an inactive conformation to an active conformation or bias IR toward an active conformation.

The invention includes a method of drug design including using at least one of the structural coordinates from each of cam-loop segment and the L1 surface listed in Table 2 to determine whether a compound interacts with the cam of IR or a fragment or derivative thereof having IR activity and is capable of changing IR from an inactive conformation to an active conformation or biasing IR toward an active conformation. A variation of the method of agonizing IR includes administering to a mammal a compound that fits spatially into the cam of IR, the compound interacting with at least one of the residues and approximate structural coordinates of the cam-loop segment and the L1 surface listed in Table 2; wherein the compound is capable of changing IR from an inactive conformation to an active conformation or biasing IR toward an active conformation.

The method can further include:
a) introducing into a computer program information defining a cam conformation including at least one residue from the Cam-loop segment in Table 2 and at least one residue from the L1 surface in Table 2, wherein the program displays the structure thereof and its relation to other IR domains;
b) comparing the structural coordinates of the compound to the structural coordinates of the cam and determining whether the compound interacts with the cam and is capable of changing IR from an active conformation to an inactive conformation;

wherein the ability to change IR from an active conformation to an inactive conformation is predictive of the ability of the compound to antagonize IR activity. The method can additionally include preparing the compound that interacts with the cam and determining whether the test compound antagonizes IR activity in an IR activity assay.

The invention also includes a method of identifying a compound which antagonizes IR or a fragment or derivative thereof having IR activity, the IR, fragment or derivative including a cam with at least one of the residues and approximate structural coordinates of the cam-loop segment and the L1 surface listed in Table 2, the method including the steps of:
a) providing the coordinates of the cam to a computerized modeling system;
b) identifying compounds which interact with the cam and change IR from an active conformation to an inactive conformation or bias IR toward an active conformation.

Another variation of the invention includes a method of producing an IR modulator including using at least one of the structural coordinates from each of cam-loop segment and the L1 surface listed in Table 2 to determine whether a compound interacts with the cam of IR or a fragment of IR or derivative thereof having IR activity and is capable of changing IR from an active conformation to an inactive conformation or biasing IR toward an active conformation.

The method of antagonizing IR can include administering to a mammal a compound that interacts with the cam of IR, the compound interacting with at least one of the residues and approximate structural coordinates of the cam-loop segment and the L1 surface listed in Table 2; wherein the compound is capable of changing IR from an active conformation to an inactive conformation or biasing IR toward an active conformation. The ability of the compound to interact with the cam can be determined by comparing the structural coordinates of the compound with the structural coordinates of IR. In the method of the invention, wherein the ability of the compound to change the conformation of IR can be determined by comparing the structural coordinates of the compound with the structural coordinates of IR.

The methods of the invention may use free IR or IR bound to insulin in an IR:insulin complex.

Another aspect of the invention includes a computer medium having recorded thereon data of an IR receptor, said data sufficient to model all or part of the quaternary structure of the receptor. The data can comprise structural coordinates of an IR receptor, the coordinates sufficient to model all or part of the quaternary structure of the receptor. The quaternary structure of the receptor can include substantially all of the quaternary structure of the receptor.

The invention also includes an insulin analog or other analog or mimetic identified by the methods of the invention.

The invention also includes a method of identifying agonists of IR by rational drug design including: producing an agonist for IR that will interact with amino acids in the IR ligand binding site or IR cam based upon the structure coordinates of the IR:insulin complex. The method of may further include synthesizing the agonist and determining whether the agonist agonizes the activity of IR in an in vivo or an in vitro assay. In a method of the invention, the quaternary structure of the IR:insulin complex can be obtained from an IR: insulin complex prepared for EM. The coordinates of the IR:insulin complex may be obtained by means of fitting atomically known subdomains into the quaternary complex.

The agonist can be designed to interact with at least one amino acid in monomer A in Table 1 and at least one amino acid in monomer B in Table 1 and cause IR to change from an inactive conformation to an active conformation or bias IR toward an active conformation.

The method of identifying a compound that modulates insulin receptor and insulin interactions or activity, can include:
a) designing a compound for modulating insulin receptor activity based upon fitted quaternary structure (eg fitting atomically known subdomains into quaternary structure) of insulin receptor bound to insulin.

The method can further synthesizing the compound and determining whether the compound modulates the interactions or activity of the insulin receptor and insulin.

Another aspect of the invention includes a method of identifying a compound that modulates insulin receptor and insulin interactions or activity, including:
a) comparing a compound for modulating insulin receptor activity to the quaternary structure of insulin receptor bound to insulin to determine whether the compound is likely to modulate insulin receptor and insulin interactions or activity;
b) determining whether the potential compound modulates the interactions or activity of the insulin receptor and insulin.

The compound may agonize or antagonize insulin receptor and insulin interactions or activity The method of identifying how a compound interacts with IR activity may include comparing the compound to all or part of the fitted quaternary structures of IR. Another aspect of the invention includes a computer readable medium including all or part of the fitted quaternary structure of IR as shown in a figure or described in the application.

Another aspect relates to an insulin analog identified by a method of the invention. The invention includes a method of agonizing insulin receptor including administering a an effective amount of the analog. The invention also includes a method of medical treatment of diabetes or hyperglycemia including administering to a mammal having diabetes or hyperglycemia a pharmaceutical composition including an effective amount of the analog. Mimetics or other insulin variants may also be used.

BRIEF DESCRIPTION OF THE DRAWINGS

Preferred embodiments are described in relation to the drawings, in which:

FIG. 3B, side view, 0; for ribbon structure see FIG. 7A). One insulin molecule (ribbon, PDB: 1 BEN) inserted with its receptor-binding domain contacting the L1-Cys-rich domains of one subunit and the L2 domain of the other. The Nanogold marker on Phe1 of insulin B chain positioned to coincide with the high-density site of reconstruction. C) Right angle side view of (B) (cf. FIG. 3B, side view 90) with L1-Cys-rich-L2 domains (insulin partly hidden), fitted TK structure in symmetric bottom domains (ribbon, PDB: 1IRK) and two dimeric FnIII structures as symmetric outer structures at mid height (ribbons, PDB: 1 mFn). Activation loop (ribbon) of left TK domain is shown in its crystallographic position. A-loop of symmetry-related right TK domain extended to overlap peptide substrate position of opposite TK in peptide-bound state (4). See also (D). D) Right angle top view of (B) (cf. FIG. 3B, top view) showing the positions of the FnIII domains (top and bottom) and the TK domains across centre. Crystallographic position of activation loop is uppermost within one TK domain, while extended activation loop of the other TK domain is below centre. One square in the wire mesh is 6.5 Å.

FIG. 5 a Three-dimensional structure of the human insulin receptor reconstructed images of the purified dimeric insulin receptor complexed with insulin obtained via low dose scanning transmission cryomicroscopy [1]. Density threshold at 85% of total volume to show contiguity of structure. Maximum diameter is 150 Å. Various regions of one αβ monomer of the dimeric structure labelled as determined from insulin location, connectivity, mass distribution and fitting of known subdomain structures. (i), View as seen from the exterior of the cell, down the two-fold symmetry axis of the $(\alpha\beta)_2$ heterodimer. Partially transparent gray disc represents cell membrane with fainter regions of structure on distal side of membrane. (ii), View at right angles to A with extracellular components above gray translucent symbolic cell membrane. (iii), View from interior of cell with fainter structures on distal (exterior) side of modelled membrane. Arrow head points to cam-like feature (see text). For domain abbreviations see FIG. 6.

b Simplified, stylized model of insulin-IR in the same orientations as FIG. 5a. (i), View from exterior of cell. (ii), Side view (cell membrane edge-on). (iii), View from interior of cell. Corresponding subdomains for one αβ monomer are indicated. The other αβ monomer is symmetrically related. Stylized catalytic regions and activation loops (spheres and hairpins) are indicated on TK domains. The two α—α disulphide bonds (1, 2) modelled on two-fold axis in strained configuration. Cams (arrow head, discs) in position permissive for transactivation. Insulin ligand represented as disc. For domain abbreviations see FIG. 6.

c Stylized model of IR in the absence of insulin. Same orientations as FIG. 5b. (i), View from exterior of cell, with separated L1-Cys-rich domains. (ii), Side view (cell membrane edge-on). (iii), View from interior of cell, with separated TK domains. Activation loops (arrow) do not reach catalytic loops (spheres on TKs). Cams (arrow head, discs) in position to block mutual approach of Fn2/TM/TK assemblies. Pair of Cys—Cys bonds (1, 2, yellow) in relaxed equilibrium positions. Insulin (disc) in position to bind to one αβ monomer. For domain abbreviations see FIG. 6.

FIG. 6

Sequential spatial arrangement of the subdomains of one αβ monomer of the insulin receptor deduced from the 3D structure [1]. The N-terminal of the α subunit (SEQ ID NO:16) is at the top, the C-terminal of the β subunit (SEQ ID NO:17) near the bottom. The domains and their delimiting amino acid sequences [5] are: αN-terminal-1-L1-158/159-cysteine-rich (CR)-310/311-L2-470/471-connecting-domain/αFibronectin0 (CD/Fn0)-572/573-αFibronectin1 (αFn1)-661/662-α-insert-domain (ID)-719-αC-terminal; βN-terminal-724-β-ID-779/780-βFn1-816/817-βFn2-913/914-juxtamembrane-929/930-transmembrane (TM)-952/953-juxtamembrane-977/978-tyrosine-kinase (TK)-1283/1284-C-terminal region-1388-βC-terminal. Other important residues are Cys524 (denoted by "1"), which forms an α—α bond on the two-fold symmetry axis, as does one of Cys682, Cys683 or Cys685 (shown as "2"). An α-β bond is formed by Cys647 in Fn1 of the α subunit (SEQ ID NO:16) and Cys872 in Fn2 of the β subunit (SEQ ID NO:17) (shown as "3"). "x" marks the cleavage site between the α (SEQ ID NO:16) and β (SEQ ID NO:17) subunits in the pro-receptor. The catalytic loop and the activation loop (shown as "A–C"; residues 1130–37 and 1149–70, respectively) are approximately in the central region of the tyrosine kinase structure [10,11].

Figure 7:
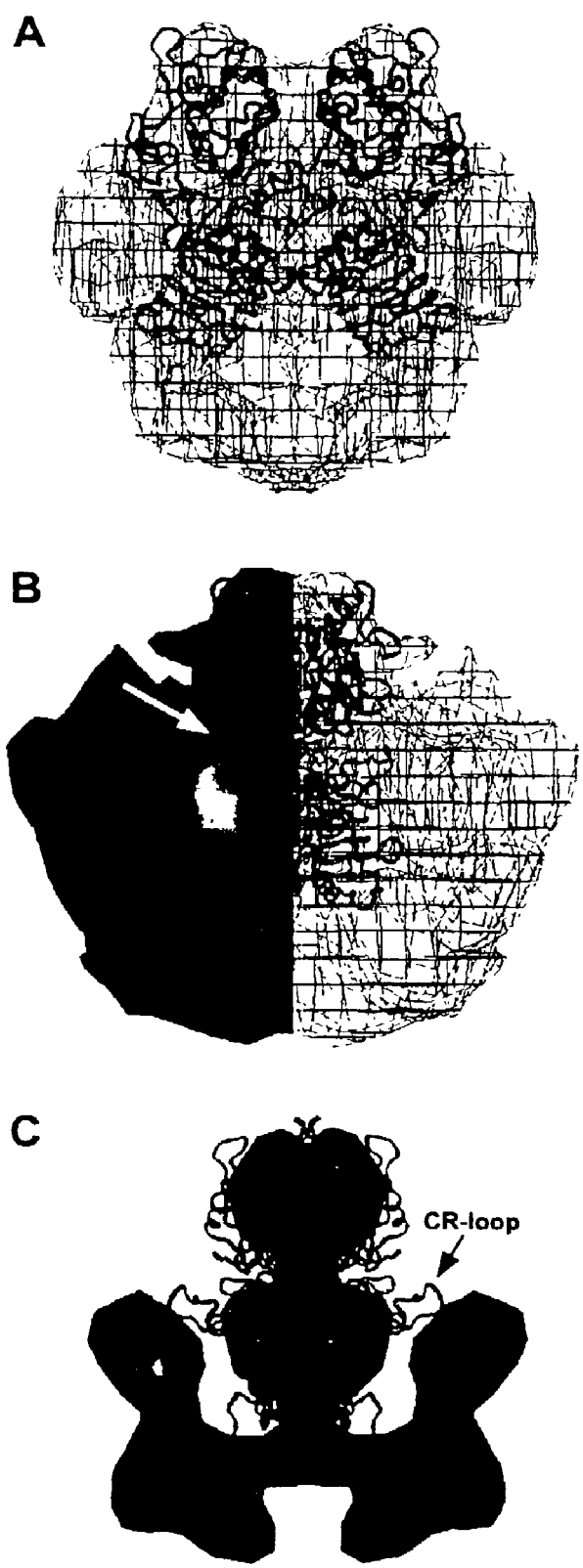
Figure 8:

FIG. 7 a Side view of IR dimer structure at volume corresponding to total receptor mass, in wire mesh representation rotated 90° with respect to 5a(ii), fitted centrally with two L1-CR-L2 regions of IR as adapted from the co-ordinates of the corresponding IGF-1R structure. Amino acid backbone representation. The diamond-shaped opening is the modelled insulin binding site with one Nanogold-insulin fitted into the site (see FIG. 8).

b End view of full-mass representation of IR dimer. Left half: surface rendering; right half: wire mesh representation. Fitted structure of two IR-adapted L1-CR-L2 regions. Arrow: cam-like region on CR domain.

c Higher density solid surface representation slightly rotated of view in FIG. 7b showing location of CR cam regions of atomic structure against Fn2 domains of 3D reconstruction.

FIG. 8 a View in parallel stereo representation of IR insulin-binding region of docked L1-CR-L2 regions (cf. FIG. 7a) fitted with insulin. Backbone representation except for amino acid sidechains tabulated in Table 1. See text for details.

b Insulin contacts with one L1-CR-L2 monomer. Slight rotation from FIG. 8a. The gold sphere represents the Nanogold label on insulin used in the 3D reconstruction. See text.

c Insulin contacts with second L1-CR-L2 monomer.

FIG. 9

Simplified schematic of structural changes during activation of insulin receptor. a. Inhibitory state. Ectodomain of dimeric α subunits (SEQ ID NO:16) each with two differing insulin binding sites and blocking cam. Unbound bivalent insulin. β subunits (SEQ ID NO:17) resting against cams, crossing membrane, with tyrosine kinase (TK) domains separated. Arrows indicate thermally induced motion. b, Insulin bound state. Blocking cams rotated, β subunits (SEQ ID NO:17) resting against centre of ectodomain. TK domains juxtaposed for transphosphorylation.

FIG. 10

A. Views (parallel stereo) of fibronectin domains docked into ectodomain quaternery structure of IR. Fn0/CD and αID regions are modelled as extending around L2 to the central 2-fold symmetry axis to form α—α disulphide bonds. The α-β disulphide is shown between αFn1 and Fn2. The domains of one αβ monomer only are labelled for identification. For clarity, LCL is shown only with part of the CR domain and all of the L2 domain (amino acids 250 to 470).

B. Complete fit of known IR and IR-like domains as docked into 3D EM reconstruction of quaternary structure of IR dimer. The TM and juxtamembrane domains, of unknown structure, have been modelled as helix and loop structures and arbitrarily placed to connect the Fn and TK domains. The unknown structures of the βID region at the N-terminal of the βFn1 domain and the C-terminal β-domain joined to the TK domains have not been modelled.

FIG. 11

Sequence of (a) human insulin (SEQ ID NO:9 and SEQ ID NO:10) (b) cow insulin (SEQ ID NO:11 and SEQ ID NO:12) (c) pig insulin (SEQ ID NO:13 and SEQ ID NO:14).

FIG. 12

Sequence of human insulin receptor (SEQ ID NO:15, SEQ ID NO:16 and SEQ ID NO:17).

FIG. 13

System for molecular modeling.

DETAILED DESCRIPTION OF THE INVENTION

The invention includes new 3D structures for dimeric two state-receptors that are activated or inhibited by ligand binding. It also includes aspects such as the ligand binding site, binding domains, other functional or structural domains and the mechanism of action of the receptors. The invention also includes methods of using these aspects to identify compounds capable of modulating (agonizing or antagonizing) the receptors.

In one embodiment, the receptor is the insulin receptor (amino acid sequence is shown in FIG. 12). In a preferred embodiment the structure is the fitted quaternary structure of IR. The "fitted quaternary structure" of IR includes the structure of the IR domains fitted together to arrive at a three-dimensional arrangement that fits into the corresponding portion of the quaternary structure of IR. Parts of the fitted quaternary structure are also useful in the methods of the invention. Prior to this invention, the 3D structure of the receptor and its mechanism of activity were unknown. The relative positions of amino acids which bound insulin and provided receptor activity were also poorly understood. The invention details the atomic interactions of insulin with the dimeric insulin receptor (IR) in the extracellular insulin binding site of the receptor. Furthermore, a mechanism is detailed which shows how this binding of insulin results in transmembrane signalling to activate the intracellular intrinsic tyrosine kinase of the insulin receptor dimer. The structure and mechanism explain the normal function of the insulin receptor as well as the effect of mutations and of altered physiological conditions. The invention provides the first comprehensive description of insulin binding to insulin receptor and the mechanical mechanism of insulin receptor activity. The structure of IR has been determined while complexed to insulin and has been modeled in the insulin-free state.

The invention includes the structure of insulin receptor fitted with the atomic coordinates of the amino acids comprising the receptor, the use of that structure to solve the structure of insulin receptor isoforms, homologues and other forms of insulin receptor, mutants and co-complexes of insulin receptor, and the use of the insulin receptor structure and that of its isoforms, homologues, mutants, and co-complexes to design modulators. The structure is particularly useful for development of ingestible (preferably oral) insulin mimicking agents (analogs, mimetics) that can be used in place of insulin (which has to be administered by injection) to treat insulin-dependent diabetes.

In one aspect the present invention is directed to the three-dimensional structure of an isolated and purified IR polypeptide and its structure coordinates. Another aspect of the invention is to use the structure coordinates of the insulin receptor to reveal the atomic details of the ligand binding site and one or more of the accessory binding sites of insulin receptor such as a cam. The entire receptor may be used or particular regions of interest may be used. Structural and conformational changes induced in the receptor may also be studied. Another aspect of the invention is to use the structure coordinates of an insulin receptor to solve the structure of a different insulin receptor or a mutant, homologue or co-complex of insulin receptor. A further aspect of the invention is to provide insulin receptor mutants characterized by one or more different properties compared to wild-type insulin receptor. Another aspect of this invention is to use the structure coordinates and atomic details of insulin receptors or mutants or homologues or co-complexes thereof to design, evaluate (preferably computationally), synthesize and use modulators of insulin receptor that prevent or treat the undesirable pathologies of inadequately or improperly functioning insulin receptor.

The IR structure of the present invention includes the three dimensional structure of the receptor including the fitted quaternary structure. The IR structure includes the ligand binding site that includes the amino acid residues listed in Table 1 and the cam structures including the amino acid residues in Table 2.

This invention also provides the first rational drug design strategy for modulating IR activity. It includes methods for identifying compounds that can interact with insulin receptor. The method for identifying insulin mimetics and insulin antagonists preferably include fitting the crystal structures, NMR structures and other structures of insulin receptor domains into the quaternary structure of the complete insulin-bound dimeric insulin receptor determined from electron microscopic image reconstruction. These interactions can be easily identified by comparing the structural, chemical and spatial characteristics of a test compound to the three dimensional structure of the insulin receptor. Since the amino acids that are responsible for receptor activity and binding were identified by this invention, drug design may be done on a rational basis. Structures such as a cam or a ligand binding site may be studied together or separately. Fragments of a cam or a ligand binding site may also be studied (e.g. at least one or at least 2 of the amino acids in table 1 or 2, optionally also including one or more proximate amino acids).

The structure serves as a detailed basis for the design and testing of insulin analogs, mimetics and insulin antagonists, initially in the computer, but also in vitro in cell culture and in vivo, providing a method for identifying modulators (antagonists and agonists) having specific contacts with the insulin receptor or an isoform, homologue, mutant or co-complex. The effect of a modification to insulin may be readily viewed on a computer, without the need to synthesize the compound and assay it in vitro. As well, non-protein organic molecules may also be compared to the insulin receptor on a computer. One can readily determine if the molecules have suitable structural and chemical characteristics to interact with, and activate or inhibit, receptor activity. The invention includes the IR modulators discovered using all or part of an IR structure of the invention (preferably the fitted quaternary structure) and the methods of the invention.

Drug Design

The determination of the quaternary structure of IR, and in particular its fitted quaternary structure, provides a basis for the design of new and specific compounds for the diagnosis and/or treatment of IR-related pathologies ("pathology" includes a disease, a disorder and/or an abnormal physical state preferably characterized by either (i) inadequate or excessive insulin in a mammal (preferably a human) or inadequate or excessive IR (SEQ ID NO:15, SEQ ID NO:16 and SEQ ID NO:17) activity. IR related pathologies include those involving IR as in FIG. 12 or IR variants described in this application.). This structure is useful in the design of modulators (agonists or antagonists), which may be used as therapeutic or prophylactic compounds for treating pathologies in which upregulation or downregulation of receptor activity is beneficial. It will be apparent that methods using IR described below may be readily adapted for use with a fragment of IR or an IR variant.

The characterization of the novel IR ligand binding site and cams permit the design of potent, highly selective IR modulators. Several approaches can be taken for the use of the IR structure in the rational design of ligands of IR. A computer-assisted, manual examination of a ligand binding site or cam structure may be done.

This invention includes the methods for identifying modulators of IR that act on the IR quaternary structure (preferably the fitted quaternary structure), ligand binding site and/or cam, as well as the modulators themselves. The agonist modulators upregulate IR activity by biasing IR towards its active, closed conformation. The antagonist modulators downregulate IR activity by biasing IR towards its inactive, open conformation. Such modulators may bind to all or a portion of the ligand binding site of IR. They may also modulate IR activity by interacting with other portions of IR, such as the cam structures. One may also select an IR amino acid (for example from the IR binding site) to which one could make a mating amino acid on insulin. Such a new amino acid on insulin would not necessarily have to be in the same category as the native amino acid, but could switch categories to be more attractive to the mating amino acid on the receptor surface. Amino acids are usefully changed in kind (eg. hydrophobic to hydrophilic, non-polar to polar, non-polar to charged, etc.) to create a new interaction between amino acids that are not already used in insulin:IR interactions, or to change the character of an existing insulin: IR interaction. For example, changes in interactions may increase or decrease the strength of the total binding, or make the insulin:IR complex less sensitive to ionic conditions around the receptor.

One example is B23 Gly on insulin that is near Ser85 (5.4 Angstr. C alpha to C alpha) and near Arg114 (9.1 Angstr. C-alpha to C-alpha) on the receptor. If B23 Gly on insulin is changed to Thr or Tyr it hydrogen-bonds to Ser85. If it is changed to Glu or Asp, it forms a salt bridge with Arg114.

A change in an amino acid that is already used may also be made, e.g. B22 Arg on insulin is near Glu285 (and others in our Table I) to form a salt bridge (electrostatic interaction). It is also near Thr325 and Ser326 on the receptor. Thus if it were changed to an amino acid such as Thr, Ser, Tyr, His etc (a hydrogen bond donor or acceptor) then this new amino acid forms a hydrogen bond with Thr325 or Ser326 to change the character of the interaction.

The methods preferably include (a) introducing into a computer program information defining all or part of IR and insulin, for example portions including the IR ligand binding site (other regions of IR described in this application, such as the cam-loop segment and L1 surface, may also be used), so that the program displays the quaternary structure thereof; b) comparing the structural coordinates of the compound to the structural coordinates of the ligand binding site and determining whether the compound fits spatially into the ligand binding site and is capable of changing insulin receptor from an active conformation to an inactive conformation or biasing insulin receptor toward an inactive conformation. The ability to change insulin receptor from an active conformation to an inactive conformation or bias insulin receptor toward an inactive conformation is predictive of the ability of the compound to antagonize insulin receptor activity.

One may also adapt the above method to determine whether the compound is capable of changing insulin receptor from an inactive conformation to an active conformation or biasing insulin receptor toward an active conformation. The ability to change insulin receptor from an inactive conformation to an active conformation or bias insulin receptor toward an active conformation is predictive of the ability of the compound to agonize insulin receptor activity.

The methods preferably further include preparing the compound and determining whether the test compound agonizes or antagonizes insulin receptor activity in an insulin receptor activity assay. Other methods described in this application may also be readily adapted and used.

The modulators may be competitive or non-competitive modulators. Once identified and screened for biological activity, these modulators may be used therapeutically or prophylactically to affect IR activity.

The invention also includes methods of agonizing or antagonizing insulin receptor by administering compounds with structural and chemical properties that allow the compounds to interact with insulin receptor residues in order to modulate receptor activity.

Interaction of Modulators of IR Ligand Binding Site

A test compound that is a modulator interacts with at least one insulin receptor residue listed in Table 1 on monomer A and at least one residue in Table 1 on monomer B in order to activate or inhibit insulin receptor. "Interact" refers to binding to the receptor which is capable of modulating its activity. Receptor fragments may be used in the methods of the invention to predict how the full receptor will react to a modulator. Since the IR is a 2-fold symmetric dimer structure, either one of the IR monomers can represent monomer A, the other representing monomer B. A modulator that is an agonist is capable of changing the IR from an inactive conformation to an active conformation. A modulator that is an antagonist is capable of changing the IR from an active conformation to an inactive conformation (or may keep or maintain IR in its inactive conformation). A modulator may bias the receptor towards a particular conformation instead of (or in addition to) changing the conformation.

The compound may also interact with at least: two, three, or four or five of the residues on each of monomer A or monomer B that are listed in Table 1. The test compound may interact with at least about: five, six, seven or eight, nine, ten, eleven or twelve amino acid residues on monomer B. The intersidechain distances between the modulator and the IR are preferably about those distances (or at least one of the distances) listed in Table 1. The distances may be varied by plus or minus about: 0.1 A, 0.2 A, 0.25 A, 0.3 A, 0.4 A, 0.5 A, 0.6 A, 0.7 A, 0.75 A, 0.8 A, 0.9 A, 1 A or >1 A, >1.5 A or 2 A as long as the test compound is still able to interact with IR and modulate its activity. It is apparent that the test compound must be able to make appropriate interactions with the IR ligand binding site if it is to activate the IR.

TABLE 1

Modeled Approaches between Insulin Side Chains and Insulin Receptor Side Chains

| Insulin Residue | Insulin Receptor Residue | (Region) | Intersidechain Distance (Å) | Interaction |
|---|---|---|---|---|
| | Monomer A | | | |
| GluA4‡ | Arg86 | (L1) | 2.5† | electrostatic |
| ThrA8 | | | 2.6 | polar |
| GluA17 | Arg331 | (L2) | 2.5 | electrostatic |
| AsnA21 | Ser323 | (L2) | 5.3* | H-bond ladder |
| LysB29 | Asp12 | (L1) | 2.6 | electrostatic |
| | Gln34 | | 2.5 | polar |
| | Monomer B | | | |
| SerB9 | Gln34 | (L1) | 2.8 | H bond |
| HisB10 | Arg14 | | 5.0* | electrostatic (H2O bridge) |
| GluB13 | Arg86 | | 2.5 | electrostatic |
| ValB12 | Phe89 | (L1) | 2.5 | hydrophobic patch |
| LeuB17 | | | 2.5 | hydrophobic patch |
| TyrB16 | Leu87 | | 2.5 | hydrophobic patch |
| PheB24 | Phe88 | | 2.5 | hydrophobic patch |
| PheB25 | | | | hydrophobic patch |
| TyrB26 | Tyr91 | | | hydrophobic patch |
| GluB21 | His247 | (CR) | 2.5 | electrostatic |
| | Gln249 | | 2.5 | polar |
| ArgB22 | Glu250 | | 4.0* | electrostatic |
| | | | 2.5 | electrostatic |
| | Glu287 | (L2) | 2.5 | electrostatic |
| | His247 | | 2.5 | electrostatic/ polar |
| GlnA5 | Arg331 | (L2) | 2.5 | polar |
| GlnA15 | | | 2.5 | polar |

‡Potential vicinal interactions are grouped
†Minimum distance of approach modelled at 2.5 Å
*Closest approach; interaction would require a water molecule, hydrogen bond chain or a rotation of the entire L2 region acids that are involved in insulin binding include: 12, 14, 15, 34, 36, 39, 64, 86 89, 90, 91, 243–251, 323 and 707–716. Only amino acids 707–716 are not in the L1-CR-L2 domains. All others are either in the walls lining the ligand binding site tunnel or are at the entrance of the ligand binding site.

Some examples of insulin derivatives and Humalog derivatives are provided below.

TABLE 1A

Table with Insulin Derivative Products

| Insulin Residue | Substitutions for Insulin Amino Acid Residue |
|---|---|
| A chain | |
| GluA4‡ | acidic amino acids ($X_1$): Asp |
| GlnA5 | hyrophilic amino acids ($X_2$): Thr, Gln, Ser, Thr, Tyr |
| ThrA8 | hyrophilic amino acids ($X_3$): Asn, Gln, Ser, Thr, Tyr |
| GlnA15 | hyrophilic amino acids ($X_4$): Thr, Gln, Ser, Thr, Tyr |
| GluA17 | acidic amino acids ($X_5$): Asp |
| AsnA21 | hyrophilic amino acids ($X_6$): Thr, Gln, Ser, Thr, Tyr |
| B chain | |
| SerB9 | hydrophilic amino acids ($Z_1$): Asn, Gln, Thr, Tyr |
| HisB10 | basic amino acids ($Z_2$): Lys, Arg |
| ValB12 | hydrophobic ($Z_3$): Ala, Leu, Ile, Pro, Phe, Trp, Met, Cys, Gly |
| GluB13 | acidic amino acids ($Z_4$): Asp |
| TyrB16 | hydrophilic amino acids acids ($Z_5$): Thr, Gln, Ser, Thr, Asn |
| LeuB17 | hydrophobic amino acids ($Z_6$): Ala, Val, Ile, Pro, Phe, Trp, Met, Cys, Gly |
| GluB21 | acidic amino acids ($Z_7$): Asp |
| ArgB22 | basic amino acids ($Z_8$): Lys, His |
| PheB24 | hydrophobic amino acids ($Z_9$): Ala, Val, Ile, Pro, Leu, Trp, Met, Cys, Gly |
| PheB25 | hydrophobic amino acids ($Z_{10}$): Ala, Val, Ile, Pro, Leu, Trp, Met, Cys, Gly |
| TyrB26 | hydrophilic amino acids acids ($Z_{11}$): Thr, Gln, Ser, Thr, Asn |
| LysB29 | basic amino acids ($Z_{12}$): His, Arg |

| | | | | | |
|---|---|---|---|---|---|
| Human insulin | | | | | |
| B-chain | FVNQH | $LCGZ_1Z_2$ | $LZ_3Z_4AL$ | $Z_5Z_6VCG$ | $Z_7Z_8GZ_9Z_{10}Z_{11}TPZ_{12}T$ |
| A-chain | $GIVX_1X_2$ | $CCX_3SI$ | $CSLYX_4$ | $LX_5NYC$ | $X_6$ |
| Humalog | | | | | |
| B-chain | FVNQH | $LCGZ_1Z_2$ | $LZ_3Z_4AL$ | $Z_5Z_6VCG$ | $Z_7Z_8GZ_9Z_{10}Z_{11}TZ_{13}PT$ |
| $Z_{13}$ may be substituted with basic amino acids: His, Arg | | | | | |
| A-chain | $GIVX_1X_2$ | $CCX_3SI$ | $CSLYX_4$ | $LX_5NYC$ | $X_6$ |

Individual amino acids in insulin that are important in binding to the receptor include: A1, A4, A5, A19, A21, B12, B16, B17, B24, B25 and B26. On the insulin receptor amino Similar insulin derivatives may be made based on other insulin sequences, such as bovine insulin and pig insulin in FIG. 11.

| Bovine Insulin | | | | |
|---|---|---|---|---|
| B-chain FVNQH | LCGZ$_1$Z$_2$ | LZ$_3$Z$_4$AL | Z$_5$Z$_6$VCG | Z$_7$Z$_8$GZ$_9$Z$_{10}$Z$_{11}$TPZ$_{12}$A |
| A-chain GIVX$_1$X$_2$ | CCX$_7$SV | CSLYX$_4$ | LX$_5$NYC | X$_6$ |

X$_7$ may be substituted with a hydrophobic amino acid: Val, Phe, Ile, Pro, Leu, Trp, Met, Cys, Gly Pig Insulin

| B-chain FVNQH | LCGZ$_1$Z$_2$ | LZ$_3$Z$_4$AL | Z$_5$Z$_6$VCG | Z$_7$Z$_8$GZ$_9$Z$_{10}$Z$_{11}$TPZ$_{12}$A |
|---|---|---|---|---|
| A-chain GIVX$_1$X$_2$ | CCX$_3$SI | CSLYX$_4$ | LX$_5$NYC | X$_6$ |

The invention includes a nucleic acid molecule encoding a polypeptide of the invention as well as a host cell including the nucleic acid molecule.

Interaction of Modulators of IR Cam

The invention also provides alternative and new methods to modulate IR activity. For example, the 3D structure shows that IR has two "cams" that change the conformation of the IR from an inactive conformation to an active conformation. The existence of these cams was unknown prior to this invention. Modulators such as organic molecules (protein or non-protein) may block or activate cam movements in order to modulate the IR toward an inactive state or to an active state.

A modulator interacts with at least one insulin receptor residue listed in Table 2 on the Cam-loop segment of the Cys-rich region and at least one residue in Table 2 on the L1 surface proximate the cam-loop segment in order to activate or inhibit insulin receptor. The modulator is capable of changing the IR from an inactive conformation to an active conformation and/or biasing IR towards an active or inactive conformation.

The compound may also interact with at least: two, three, four, five or six (or seven, eight, nine, ten, eleven or twelve) of the residues listed in Table 2 on each of the Cam-loop segment of the Cys-rich region and the L1 surface proximate the cam-loop segment. The intersidechain distances between the test compound and the IR may be varied by plus or minus about: 0.1 A, 0.2 A, 0.25 A, 0.3 A, 0.4 A, 0.5 A, 0.6 A, 0.7 A, 0.75 A, 0.8 A, 0.9 A, 1 A or >1 A, >1.5 A or 2 A as long as the test compound is still able to interact with IR and modulate its activity. It is apparent that the modulator must be able to make appropriate interactions with the IR cam if it is to activate or inactivate the IR.

TABLE 2

Charged and polar amino acids in the region of the cam-loop can bind a modulator to the receptor, to allow specificity of binding, and to move or block the Cam-loop segment. All specific interactions with the amino acids below would be electrostatic (ionic) except with Gln (glutamine) and Asn (asparagine) which are polar.

| Cam-loop segment of Cys-rich region | |
|---|---|
| Lys265 | electrostatic |
| Lys267 | electrostatic |
| Asn268 | polar |
| Arg270 | electrostatic |
| Arg272 | electrostatic |
| Glu273 | electrostatic |
| L1 surface near cam-loop segment | |
| Glu1 NH$_3$$^+$ | electrostatic |
| Asn15 | polar |
| Asn16 | polar |
| Arg19 | electrostatic |
| Glu22 | electrostatic |

TABLE 2-continued

Charged and polar amino acids in the region of the cam-loop can bind a modulator to the receptor, to allow specificity of binding, and to move or block the Cam-loop segment. All specific interactions with the amino acids below would be electrostatic (ionic) except with Gln (glutamine) and Asn (asparagine) which are polar.

| Glu24 | electrostatic |
|---|---|
| Asn25 | polar |
| Glu44 | polar |
| Asp45 | electrostatic |
| Arg47 | electrostatic |
| Asp48 | electrostatic |
| Lys53 | electrostatic |

The invention includes a method of agonizing or antagonizing IR activity by administering a modulator identified according to the methods of the invention.

IR Modulating Compounds

A diagnostic or therapeutic modulating compound of the present invention can be, but is not limited to, at least one selected from a nucleic acid, a compound, a protein, a lipid, a saccharide, an isotope, a carbohydrate, an imaging agent, a lipoprotein, a glycoprotein, an enzyme, a detectable probe, and antibody or fragment thereof, or any combination thereof. Diagnostic compounds (useful in diagnosis as a research tool in an assay) can be detectably labeled as for labeling antibodies. Such labels include, but are not limited to, enzymatic labels, radioisotope or radioactive compounds or elements, fluorescent compounds or metals, chemiluminescent compounds and bioluminescent compounds. Other types of compounds may also be useful.

The compound may include an amino acid sequence (including a peptide, a polypeptide or a protein) or an amino acid sequence derivative (i.e. an analog, prepared for example by substituting, deleting, modifying (eg. glycosylating) one or more amino acids—see, for example, U.S. Pat. Nos. 5,952,297, 5,922,675, 5,700,662, 5,693,609, 5,646, 242, 5,149,777, 5,008,241, 4,946,828 and 5,164,366. The analog may also be part of a human insulin analog complex, such as that in U.S. Pat. No. 5,474,978.).

The analog may be an insulin derivative, an insulin precursor derivative or a derivative of an already known insulin analog (See for example U.S. Pat. Nos. 5,952,297, 5,922,675, 5,747,642, 5,716,927). One skilled in the art may analyze insulin, its precursors, and other known analogs to determine how they interact with IR and then prepare improved compounds.

Those of skill in the art recognize that a variety of techniques are available for constructing derivatives insulin with the same or similar desired biological activity insulin but with more favorable activity than the polypeptide with respect to route of administration, solubility, stability, and/or susceptibility to hydrolysis and proteolysis. See, for example, Morgan and Gainor, *Ann. Rep. Med. Chem.*, 24:243–252 (1989). Examples of polypeptide derivatives are described in U.S. Pat. No. 5,643,873. Other patents describing how to make and use derivatives include, for example, U.S. Pat. Nos. 5,786,322, 5,767,075, 5,763,571, 5,753,226, 5,683,983, 5,677,280, 5,672,584, 5,668,110, 5,654,276, 5,643,873. Derivatives may be designed on computer by comparing compounds to the 3D structures disclosed in this application. Derivatives of insulin may also be made according to other techniques known in the art. For example, by treating a polypeptide of the invention with an agent that chemically alters a side group by converting a hydrogen group to another group such as a hydroxy or amino group. Derivatives can include sequences that are either entirely made of amino acids or sequences that are hybrids including amino acids and modified amino acids or other organic molecules.

The compound may also be a nonprotein organic molecule, such as a mimetic (i.e. a non-protein molecule which functionally mimics a peptide, polypeptide or a protein). For example, a mimetic may functionally mimic insulin by binding to IR and activating it. Such a mimetic may activate IR to a greater or lesser extent than that caused by insulin as long as the mimetic produces the end result of IR activation. Examples of mimetics are pyrrolidine compounds such as (2R,3R,4R)-3,4-dihydroxy-2-hydroxymethylpyrrolidine and other substituted 2-methylpyrrolidines (e.g. U.S. Pat. No. 5,854,272) or hydroxy alkyl piperidine (e.g. U.S. Pat. No. 5,863,903). Small organic molecules may also be used to antagonize or agonize IR by interacting with a cam.

A compound can have a therapeutic effect on the target cells, the effect one of those known to be caused by modulation of IR. The therapeutic effects that modulates at least one IR in a cell can be provided by therapeutic agent delivered to a target cell via pharmaceutical administration (discussed below).

Determining Suitable Types of Modulators from IR Structure

One skilled in the art would recognize, in view of the fitted quaternary structure of IR, that the type of modulator used may be varied or customized according to the portion of IR targeted. For example, modulators may be simple peptides which take advantage of specific hydrophilic, hydrophobic, or charge interactions, or variously branched peptides with each branch differentially contributing to a particular interaction (such as the loligomer structures of Gariepy and co-workers: PNAS USA 92, 2056–60, 1995; Bioconjugate Chem. 10, 745–54, 1999). Modulators may be simpler chemicals with corresponding interaction sites, in or near the insulin binding contact sites of IR. Such agents may also be molecules that act external to the insulin binding site to effect activation or inhibition by interacting with specific sites identified as important in the mechanism of transmembrane signal transduction. These include specific chemicals, peptides or monoclonal and polyclonal antibodies or sub-antibody fragments such as the Fab, or Fv fragments. They include molecules that specifically remove or enhance the natural blockage on the insulin receptor to activation of its intrinsic tyrosine kinase. Such agents may also be molecules that enhance or inhibit transphosphorylation of the juxtaposing intrinsic pair of tyrosine kinase domains of the dimeric insulin receptor.

Determining Structure of IR, IR Variants and Other Receptors

Complete IR Structure

Techniques described in this application (such as those in references 4 and 5 or U.S. Pat. No. 5,834,228) were used to identify and characterize regions of an insulin receptor such as the LI-Cys-rich-L2 domain. We characterize the entire insulin receptor and its ligand binding site using these techniques. The fitted quaternary structure of IR needed for drug design is disclosed in this application.

IR Variants and Other Receptors

The IR data of the invention may be also used to solve the structure of IR variants (eg. mutants, homologs) or other dimeric receptors, or of any other protein with significant amino acid sequence homology to any functional or structural domain of IR. We determine the structure of IR as well as mutants. IR has two isoforms, A and B. Isoform A is shorter than isoform B by 12 amino acids which are coded by exon 11 of the IR gene (the twelve amino acids are from Lys718 to Arg 729 as follows: Lys-Thr-Ser-Ser-Gly-Thr-Gly-Ala-Glu-Asp-Pro-Arg). Isoform A interacts with insulin and produces the same effect as isoform B, which is a metabolic effect.

The insulin receptor described in this application was extracted from human placenta. Insulin receptor from other sources, such as other tissues, cells or cDNA may also be modeled and used in the methods of the invention. The techniques described in this application to image the receptor may be used with insulin receptor from any human, mammalian or other tissue. Insulin receptor homologues and other forms of insulin receptor, mutants and co-complexes of insulin receptor may also be used. A fragment of the receptor may also be used. A fragment may be from about 25–50, about 50–100, about 100–250 or about 250–500, 500–1000 or at least about 1000 amino acids.

The IR is similar to other dimeric receptors, such as IGFR and IRR. The 3D structure of IR may be used to determine the 3D structure of these receptors by identifying regions of homology (similarity between amino acid, secondary, tertiary or quaternary structure) between the receptors and determining the structure of the dimeric receptor.

One useful method for this purpose is molecular replacement in crystallography. In this method, the unknown structure in a crystal, whether it is another form of IR, an IR mutant, or the structure of some other dimeric receptor with significant amino acid sequence homology to any functional domain of IR, may be determined using the IR structure coordinates of the IR dimer structure coordinates of this invention. This method will provide an accurate structural form for the unknown structure more quickly and efficiently.

Computer Based Design

The invention allows computational screening of molecule data bases for compounds that can bind in whole, or in part, to IR. The IR structure of the invention permits the design and identification of synthetic compounds and/or other molecules which have a shape complimentary of the conformation of the IR ligand binding site of the invention. Using known computer systems, the coordinates of the IR structure of the invention may be provided in machine readable form, the test compounds designed and/or screened and their conformations superimposed on the complementary surface structures and surface characteristics of the receptor or of its binding site. Subsequently, suitable candidates identified as above may be screened for the desired activity, stability, and other characteristics.

In this screening, the quality of fit of such entities or compounds to the binding site may be judged either by shape complementary (R. L DesJarlais et al. *J. Med. Chem* 31:72–729 (1988) or by estimated interaction energy (E. C. Meng et al, J. Comp. Chem. 13: 505–524 (1992)].

Thus, the IR structure permits the screening of known molecules and/or the designing of new molecules which bind to the IR structure, particularly at the ligand binding site or cams, via the use of computerized evaluation systems. For example, computer modeling systems are available in which the sequence of the IR, and the IR structure (i.e., atomic coordinates of IR and/or the atomic coordinate of the ligand binding site cavity, bond angles, dihedral angles, distances between amino acids in the ligand binding site region, etc. as provided by the fitted quaternary structure may be input. A machine readable medium may be encoded with data representing the coordinates of the entire IR structure. The computer then generates structural details of the site into which a test compound should bind, thereby enabling the determination of the complementary structural details of said test compound.

The production of compounds that bind to or modulate IR generally two factors. First, the compound must be capable of physically and structurally associating with IR. Non-covalent molecular interactions important in the association of IR with its substrate include hydrogen bonding, ionic interactions van der Waals interactions and hydrophobic interactions.

The invention permits the design of agents that bind to the three dimentional surfaces of IR by using the pattern on those surfaces of positive charges, negative charges, hydrophobic grouping of atoms, dipolar groups and hydrodren bonds that are revealed in the structure of the surfaces and in the relative positioning of these surfaces with respect to each other in the quaternary structure.

Those skilled in the art can create an agent that places the positions of chemical groups on the agent near matching atoms or groups of atoms on IR using well-known interactions such those as in Table 3.

TABLE 3

| Characteristics of atoms or groups of atoms on IR | Matching characteristics of atoms or groups of atoms on the agent |
| --- | --- |
| positive charge | negative charge |
| negative charge | positive charge |
| hydrophobic group | hydrophobic group |
| polar group | polar group |
| hydrogen donor | hydrogen acceptor |
| hydrogen acceptor | hydrogen donor |

Second, the compound must be able to assume a conformation that allows it to associate with IR. The compound will preferably interact with the ligand binding site or a cam and bias or change IR towards either an active conformation or inactive conformation. Although certain portions of the compound will not directly participate in this association with IR those portions may still influence the overall conformation of the molecule. This, in turn, may have a significant impact on potency. Such conformational requirements include the overall three-dimensional structure and orientation of the chemical entity or compound in relation to all or a portion of the binding site, e.g., ligand binding site, accessory binding site, or cam of IR or the spacing between functional groups of a compound comprising several chemical entities that directly interact with IR.

The potential modulating effect of a chemical compound with IR may be estimated prior to its actual synthesis and testing by the use of computer modeling techniques. If the structure of the compound shows insufficient interaction and association between it and IR the compound is not synthesized and tested. If computer modeling indicates a suitable interaction, the molecule may then be synthesized and tested for its ability to bind to IR in an assay. Synthesis of ineffective and inoperative compounds can be avoided.

Computer modeling may be combined with assay techniques. For example, one could probe the IR (or fragments thereof) with a variety of different molecules to determine optimal sites for interaction between candidate modulators and IR. Small molecules that bind tightly to IR sites can be designed and synthesized and tested for their IR modulatory activity. This information can be combined with computer modeling information. A modulating compound may be computationally evaluated. A modulating compound may be further designed by a series of steps in which compounds or fragments are screened and selected for their ability to associate with the individual binding amino acids, secondary, tertiary or quaternary structure or other areas of IR.

One skilled in the art may use one of several methods to screen chemical entities or fragments for their ability to interact with IR. This process may begin generating the ligand binding site on the computer screen based on the IR amino acids and distances from the co-ordinates of the IR complex. Selected fragments or chemical entities are then be positioned against IR. Docking may be accomplished using software such as Insight, Quanta, and Sybyl, followed by energy minimization and molecular dynamics with standard molecular mechanics forcefields, such as CHARMM and AMBER.

Specialized computer programs may also assist in the process of selecting fragmented or chemical entities. These include:

MCSS (Molecular Simulations, Burlington, Mass.) [A. Miranker and M. Karpius. "Functionality Maps of Binding Sites: A Multiple Copy Simultaneous Search Method". Proteins: Structure, Function and Genetics, 11:29–34 (1991)].

GRID (Oxford University, Oxford, UK) [P. J. Goodford, "A Computational Procedure for Determining Energetically Favorable Binding Sites on Biologically Important Macromolecules". J. Med. Chem. 28:849–857 (1985)].

DOCK (University of California, San Francisco, Calif.) [I. D. Kuntz et al, "A Geometric Approach to Macromolecule-Ligand Interactions", J. Mol. Biol. 161: 269–288 (1982)].

AUTODOCK (Scripps Research Institute, La Jolla, Calif.) [D. S. Goodsell and A. J. Olsen, "Automated Docking of Substrates to Proteins by Simulated Annealing". Proteins: Structure, Function, and Genetics, 8:192–202 (1990)].

Additional commercially available computer databases for small molecular compounds include Cambridge Structural Database and Fine Chemical Database. For a review see Rusinko, A., Chem. Des., Auto. News 8.44–47 (1993).

For example, software such as GRID (a program that determines probable interaction sites between probes with various functional group characteristics and the enzyme surface) analyzes the ligand binding site to determine structures of modulating compounds. The program calculates, with suitable activating or inhibiting groups on molecules (e.g. protonated primary amines as the probe) suitable conformations. The program also identifies potential hot spots around accessible positions at suitable energy contour levels. Suitable ligands, such as inhibiting or activating compounds or compositions, are then tested for modulating IR.

Once suitable chemical entities or fragments have been selected, they can be assembled into a single compound. Assembly may be proceeded by visual inspection of the relationship of the fragments to each other on the three-dimensional image displayed on a computer screen in relation to the structure coordinates of IR. This would typically be followed by manual model building using software such as Quanta or Sybyl.

Useful programs to aid one of skill in the art in connecting the individual chemical entities or fragments include:

3D Database systems such as MACCS-3D (MDL Information Systems, San Leandro, Calif.). See Y. C. Martin, "3D Database Searching in Drug Design", J. Med. Chem., 35:2145–2154 (1991).

CAVEAT (University of California, Berkeley, Calif.) [P. A. Barlett et al. "CAVEAT: A program to Facilitate the Structure Derived design of Biologically Active Molecules," in *Molecular Recognition in Chemical and Biological Problems.*" Special Pub., Royal Chem. Soc. 78, pp 182–196 (1989).

HOOK (Molecular Simulations, Burlington, Mass.). Instead of proceeding to build IR modulator in a step-wise fashion one fragement or chemical entity at a time as described above, inhibitory or other type of binding compounds may be designed as whole or "de novo" using either an empty ligand binding site or optionally including some portion(s) of a known compound(s). These methods include:

LUDI (Biosym Technologies, San Diego. Calif.) [H.-J. Bohm, "The Computer Program LUDI: A New method for the De Novo Design of Enzyme Inhibitors", J. Comp, Aid Molec, Design, 6:61–78 (1992)].

LeapFrog (Tripos Associates, St. Louis, Mo.). Other molecular modeling techniques may also be used. For example, N. C. Cohen et al. "Molecular Modeling Software and Methods for Medicinal Chemistry". J. Med. Chem., 33:883–894 (1999). M. A. Navia and M. A. Murcko, "The Use of Structural Information in Drug Design", *Current Opinions in Structural Biology,* 2:202–210 (1992). For example, where the structures of test compounds are known, a model of the test compound may be superimposed over the model of the structure of the invention. Numerous methods and techniques are known in the art for performing this step, any of which may be used. See, e.g., P. S. Farmer, Drug Design, Ariens, E. J., ed., Vol. 10, pp 119–143 (Academic Press, New York, 1980); U.S. Pat. No. 5,331,573; U.S. Pat. No. 5,500,807; C. Verlinde, *Structure,* 2:577–587 (1994); and I. D. Kuntz, *Science,* 257:1078–1082 (1992). The model building techniques and computer evaluation systems described herein are not a limitation on the present invention.

LEGEND (Molecular Simulations, Burlington, Mass.) [Y. Nishibata and A. Itai, *Tetrahedron,* 47:8985 (1991)].

Using these computer evaluation systems, a large number of compounds may be quickly and easily examined and expensive and lengthy biochemical testing avoided. Moreover, the need for actual synthesis of many compounds is effectively eliminated.

Apparatus Including the IR Fitted Quaternary Structure or Other IR Structural Information Storage media for the IR fitted quaternary structure or other IR structural information include, but are not limited to: magnetic storage media, such as floppy discs; hard disc storage medium, and magnetic tape; optical storage media such as optical discs or CD-ROM; electrical storage media such as RAM and ROM; and hybrids of these categories such as magnetic/optical storage media. Any suitable computer readable mediums can be used to create a manufacture comprising a computer readable medium having recorded on it an amino acid sequence and/or data of the present invention.

"Recorded" refers to a process for storing information on computer readable medium. A skilled artisan can readily adopt any of the presently know methods for recording information on computer readable medium to store an amino acid sequence, nucleotide sequence and/or EM data information of the present invention.

A variety of data storage structures are available to a skilled artisan for creating a computer readable medium having recorded thereon an amino acid sequence and/or data of the present invention. The choice of the data storage structure will generally be based on the means chosen to access the stored information. In addition, a variety of data processor programs and formats can be used to store the sequence and data information of the present invention on computer readable medium. The sequence information can be represented in a word processing text file, formatted in commercially-available software such as WordPerfect and MicroSoft Word, or represented in the form of an ASCII file, stored in a database application, such as DB2, Sybase, Oracle, or the like. A skilled artisan can readily adapt any number of data processor structuring formats (e.g. text file or database) in order to obtain computer readable medium having recorded thereon the information of the present invention.

By providing the sequence and/or data on computer readable medium and the structural information in this application, a skilled artisan can routinely access the sequence and data to model a receptor a subdomain thereof, or a ligand thereof. As described above, computer algorithms are publicly and commercially available which allow a skilled artisan to access this data provided in a computer readable medium and analyze it for molecular modeling or other uses.

The present invention further provides systems, particularly computer-based systems, which contain the sequence and/or data described herein. Such systems are designed to do molecular modeling for an IR or at least one subdomain or fragment thereof.

In one embodiment, the system includes a means for producing a fitted quaternary structure of insulin receptor (or a fragment or derivative thereof) and means for displaying the fitted quaternary structure of insulin receptor. The system is capable of carrying out the methods described in this application. The system preferably further includes a means for comparing the structural coordinates of a test compound to the structural coordinates of the insulin receptor (or a fragment or derivative thereof, such as a cam-loop, L1 region, ligand binding site or other region described in this application) and means for determining if the test compound is capable of modulating insulin receptor between an active conformation and an inactive conformation or biasing insulin receptor toward an active or inactive conformation, as described in the methods of the invention.

As used herein, "a computer-based system" refers to the hardware means, software means, and data storage means used to analyze the sequence and/or data of the present invention. The minimum hardware means of the computer-based systems of the present invention comprises a central processing unit (CPU), input means, output means, and data storage means. A skilled artisan can readily appreciate which of the currently available computer-based system are suitable for use in the present invention.

As stated above, the computer-based systems of the present invention comprise a data storage means having stored therein our IR or fragment sequence and/or data of the present invention and the necessary hardware means and software means for supporting and implementing an analysis means. As used herein, "data storage means" refers to memory which can store sequence or data (coordinates, distances, quaternary structure etc.) of the present invention, or a memory access means which can access manufactures having recorded thereon the sequence or data of the present invention.

As used herein, "search means" or "analysis means" refers to one or more programs which are implemented on the computer-based system to compare a target sequence or target structural motif with the sequence or data stored within the data storage means. Search means are used to identify fragments or regions of an IR which match a particular target sequence or target motif. A variety of known algorithms are disclosed publicly and a variety of commercially available software for conducting search means are and can be used in the computer-based systems of the present invention. A skilled artisan can readily recognize that any one of the available algorithms or implementing software packages for conducting computer analyses that can be adapted for use in the present computer-based systems.

As used herein, "a target structural motif," or "target motif," refers to any rationally selected sequence or combination of sequences in which the sequences(s) are chosen based on a three-dimensional configuration or electron density map which is formed upon the folding of the target motif. There are a variety of target motifs known in the art. Protein targets include, but are not limited to, ligand binding sites, structural subdomains, epitopes, and functional domains. A variety of structural formats for the input and output means can be used to input and output the information in the computer-based systems of the present invention.

Figure 13:
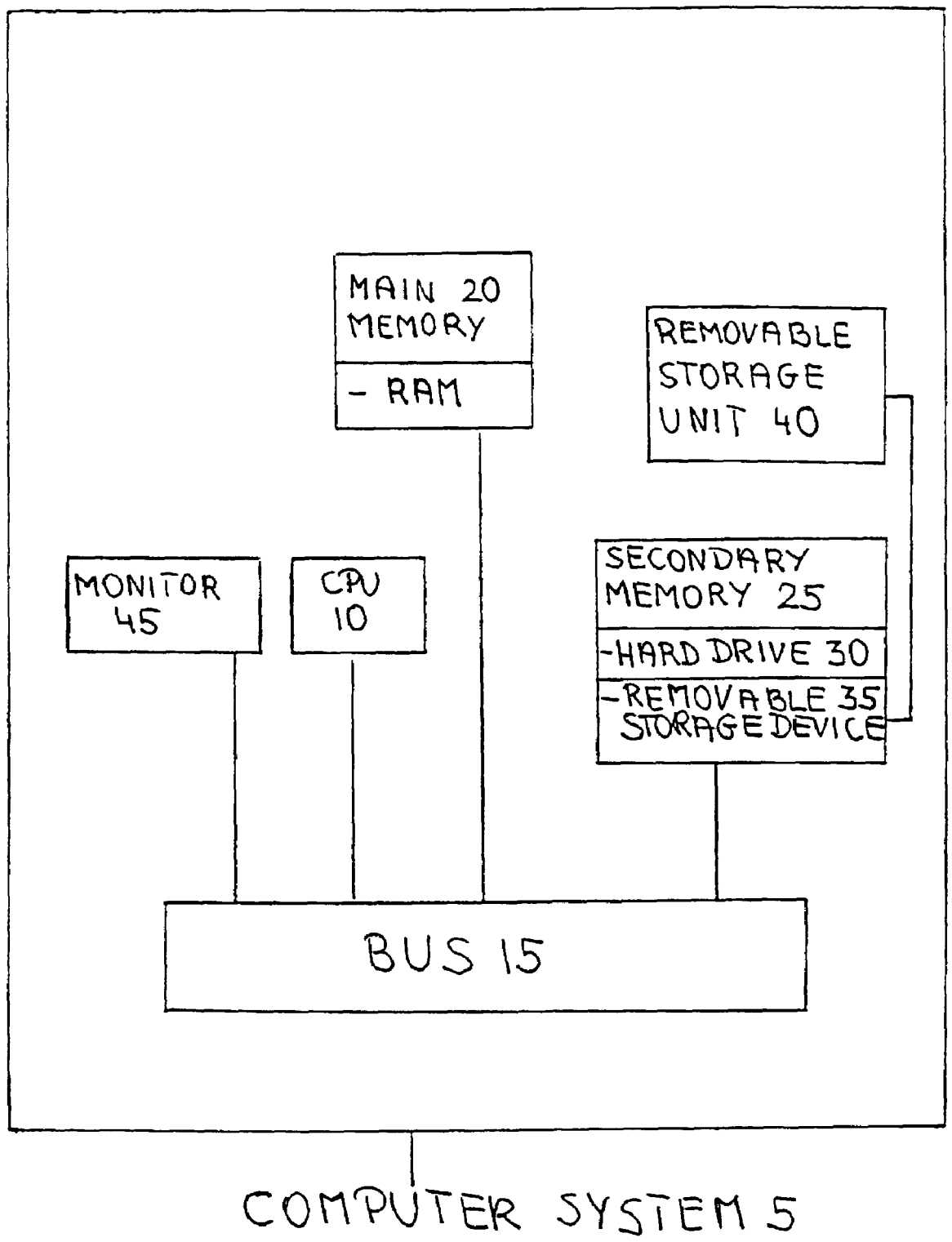

One application of this embodiment is provided in FIG. 13. This figure provides a block diagram of a computer system 5 that can be used to implement the present invention. The computer system 5 includes a processor 10 connected to a bus 15. Also connected to the bus 15 are a main memory 20 (preferably implemented as random access memory, RAM) and a variety of secondary storage memory 25 such as a hard drive 30 and a removable storage medium 35. The removable medium storage device 35 may represent, for example, a floppy disk drive, A CD-ROM drive, a magnetic tape drive, etc. A removable storage unit 40 (such as a floppy disk, a compact disk, a magnetic tape, etc.) containing control logic and/or data recorded therein may be inserted into the removable medium storage medium 35. The computer system 5 include appropriate software for reading the control logic and/or the data from the removable medium storage device 35 once inserted in the removable medium storage device 35. A monitor 45 can be used as connected to the bus 15 to visualize the structure determination data.

Amino acid, encoding nucleotide or other sequence and/ or data of the present invention may be stored in a well known manner in the main memory 20, any of the secondary storage devices 25, and/or a removable storage device 40. Software for accessing and processing the amino acid sequence and/or data (such as search tools, comparing tools, etc.) reside in main memory 20 during execution.

One or more computer modeling steps and/or computer algorithms are used as described above to provide a molecular 3-D model, preferably showing the fitted quaternary structure, of a cleaved dimeric receptor, using amino acid sequence data and atomic coordinates for the receptor. The structure of other dimeric receptors such as IGFR and IRR may be readily determined using methods of the invention and the present knowledge of these receptors.

Assays of Modulators Identified from IR Structure

Once identified, the modulator may then be tested for bioactivity using standard techniques (e.g. in vitro or in vivo assays). For example, the compound identified by drug design may be used in binding assays using conventional formats to screen agonists (e.g by measuring in vivo or in vitro binding of receptor to insulin after addition of a compound). One assay is the fat cell assay for glucose uptake and oxidation which is known in the art. Experiments may also be done with whole diabetic animals. Suitable assays include, but are not limited to, the enzyme-linked immunosorbent assay (ELISA), or a fluorescence quench assay. In evaluating IR modulators for biological activity in animal models (e.g. rat, mouse, rabbit), various oral and parenteral routes of administration are evaluated. Using this approach, it is expected that modulation of an IR occurs in suitable animal models, using the ligands discovered by molecular modeling.

Once identified and screened for biological activity, these inhibitors may be used therapeutically or prophylactically to modulate IR activity as described below.

Pharmaceutical/Diagnostic Formulations of Modulators Identified from Quaternary Structure, Methods of Medical Treatment and Uses Modulating IR in a Cell The present invention also provides a method for modulating the activity of the IR in a cell using IR modulating compounds or compositions of the invention. In general, compounds (antagonists or agonists) which have been identified to inhibit or enhance the activity of IR can be formulated so that the agent can be contacted with a cell expressing a IR protein in vivo. The contacting of such a cell with such an agent results in the in vivo modulation of the activity of the IR proteins. So long as a formulation barrier or toxicity barrier does not exist, agents identified in the assays described above will be effective for in vivo and in vitro use. These modulators may be used in therapies that are beneficial in the treatment of diabetes and other diseases, disorders and abnormal physical states characterized by improper or inadequate insulin receptor activity. Even if receptor activity is normal, there may be therapeutic benefit in upregulating or downregulating its activity in some circumstances.

Medical Treatments and Uses

Diseases, disorders and abnormal physical states that may be treated by IR agonists include diabetes and hyperlgycemia. Diseases, disorders and abnormal physical states that may be treated by IR antagonists include hypoglycemia.

Isoform A of IR is shorter than isoform B by 12 amino acids which are coded by exon 11 of the IR gene. Isoform A interacts with insulin and produces the same effect as isoform B, which is a metabolic effect. Isoform A acts as an IGF-2 receptor which may be important in the growth of cancer cells (Frasca, F, Pandini, G, Scalia, P, Sciacca, L, Mineo, R, Costantino, A, Goldfine, I D, Delfiore, A, Vigneri, R, 1999, Insulin receptor isoform A: A newly recognized high affinity insulin like growth factor II receptor in situ and cancer cells. Molecular and Cellular Biology 19:5 pg. 3278–3288.). IGF-2 acts on isoform A to produce a growth effect via IR rather than just a metabolic effect. The quaternary structure of isoform A is very similar to isoform B and can be readily determined according to the information in this application. IGF I binds to both isoforms with low affinity ($\frac{1}{10}$) and also produces a growth effect (less significant because of the low affinity binding). One may design an antagonist of isoform A that does not interact with isoform B (or at least has lower affinity binding to isoform B) to inhibit cancer cell growth in response to IGF-2.

Pharmaceutical Compositions

Modulators may be combined in pharmaceutical compositions according to known techniques. The compounds of this invention are preferably incorporated into pharmaceutical dosage forms suitable for the desired administration route such as tablets, dragees, capsules, granules, suppositories, solutions, suspensions and lyophilized compositions to be diluted to obtain injectable liquids. The dosage forms are prepared by conventional techniques and in addition to the compounds of this invention could contain solid or liquid inert diluents and carriers and pharmaceutically useful additives such as lipid vesicles liposomes, aggregants, disaggregants, salts for regulating the osmotic pressure, buffers, sweeteners and colouring agents. Slow release pharmaceutical forms for oral use may be prepared according to conventional techniques. Other pharmaceutical formulations are described for example in U.S. Pat. No. 5,192,746.

Pharmaceutical compositions used to treat patients having diseases, disorders or abnormal physical states could include a compound of the invention and an acceptable vehicle or excipient (Remington's Pharmaceutical Sciences 18$^{th}$ ed, (1990, Mack Publishing Company) and subsequent editions). Vehicles include saline and D5W (5% dextrose and water). Excipients include additives such as a buffer, solubilizer, suspending agent, emulsifying agent, viscosity controlling agent, flavor, lactose filler, antioxidant, preservative or dye. The compound may be formulated in solid or semisolid form, for example pills, tablets, creams, ointments, powders, emulsions, gelatin capsules, capsules, suppositories, gels or membranes. Routes of administration include oral, topical, rectal, parenteral (injectable), local, inhalant and epidural administration. The compositions of the invention may also be conjugated to transport molecules to facilitate transport of the molecules. The methods for the preparation of pharmaceutically acceptable compositions which can be administered to patients are known in the art.

The pharmaceutical compositions can be administered to humans or animals. Dosages to be administered depend on individual patient condition, indication of the drug, physical and chemical stability of the drug, toxicity, the desired effect and on the chosen route of administration (Robert Rakel, ed., Conn's Current Therapy (1995, W.B. Saunders Company, USA)).

Polypeptides, such as the insulin derivatives described above, may be produced for use in pharmaceutical compositions using known techniques. For example, Novolin™, a recombinant human insulin, is produced in *Saccharmyces cerevisiae*. Other host cells include any cell capable of producing the polypeptide, such as a cell selected from the group consisting of a plant, a bacterial, fungus (eg. yeast), protozoa, algal or animal cell.

One may prepare a nucleic acid molecule encoding a polypeptide designed by a method of the invention (including the insulin derivatives described above). Recombinant nucleic acid molecules include the nucleic acid molecule and a promoter sequence, operatively linked so that the promoter enhances transcription of the nucleic acid molecule in the host cell. The nucleic acid molecules can be cloned into a variety of vectors by means that are well known in the art. A number of suitable vectors may be used, including cosmids, plasmids, bacteriophage, baculoviruses and viruses. Preferable vectors are capable of reproducing themselves and transforming a host cell (Sambrook, J, Fritsch, E. E. & Maniatis, T. (1989). Molecular Cloning: A laboratory manual. Cold Spring Harbor Laboratory Press. New York; Ausubel et al. (1989) Current Protocols in Molecular Biology, John Wiley & Sons, Inc.). The methods of the invention further include preparing nucleic acid molecules, recombinant nucleic acid molecules, vectors and host cells (the invention also includes the aforementioned products themselves). The nucleic acid molecules, recombinant nucleic acid molecules and vectors are also useful for gene therapy, for example, by transforming pancreatic cells that produce insulin. Gene therapy methods and compositions are taught, for example, in U.S. Pat. Nos. 5,672,344, 5,645,829, 5,741,486, 5,656,465, 5,547,932, 5,529,774, 5,436,146, 5,399,346 and 5,670,488, 5,240,846. The method can preferably involve a method of delivering a nucleic acid molecule encoding a polypeptide of the invention to the cells of an individual having diabetes, comprising administering to the individual a vector comprising DNA encoding a polypeptide of the invention. The invention includes methods and compositions for providing a nucleic acid molecule encoding the polypeptide to the cells of a subject (preferably a human) such that expression of the nucleic acid molecule in the cells provides the biological activity or phenotype of the polypeptide to those cells. Sufficient amounts of the nucleic acid molecule are administered and expressed at sufficient levels to provide the biological activity or phenotype of the polypeptide to the cells.

EXAMPLE 1

Determination of the 3D Structure of IR

Preparation of IR

Insulin receptor protein (HIR (SEQ ID NO:15, SEQ ID NO:16 and SEQ ID NO:17)) was solubilized from human placental membranes and purified by affinity chromatography on an insulin column (9) followed by further FPLC purification on Sephacryl S-200. The purity of HIR (SEQ ID NO:15, SEQ ID NO:16 and SEQ ID NO:17) was better than 95% by sodium dodecyl sulfate polyacrylamide gel electrophoresis. HIR (SEQ ID NO:15, SEQ ID NO:16 and SEQ ID NO:17) was incubated with NG-BI (final concentration of ~0.5×10$^{-6}$ M) at 4° C. overnight in 20 mM HEPES buffer (pH 7.5) at a molar ratio of insulin:HIR of ~10:1. Free NG-BI was removed by microfiltration with a cut-off of 300 kDa (Sigma). The mixture was diluted to 7.5 µg of receptor protein/ml with 20 mM HEPES buffer, pH 7.5, prior to loading on the grid.

Preparation of Specimen for STEM

The specimen (5 µl) was injected into 5 µl of the dilution buffer on 300-mesh copper grid coated with a holey plastic film overlaid with a carbon film 23 Å thick, washed with HEPES buffer and 10 mM ammonium acetate (pH 7.5). The grid was drained by wicking with filter paper, leaving a very thin solution layer, then immediately quick-frozen by plunging into liquid ethane at −150° C. The frozen specimen was transferred at liquid nitrogen temperature into the STEM (Vacuum Generators, Model HB601UX) and freeze-dried at −140° C. in the STEM cold-stage. Images in a 480×480 pixel format were acquired with the specimen at −150° C. using cold field emission at 100 kV, a dose of 6 e/Å$^2$ and a pixel size of 6.5 Å. The beam size was 3 Å. Inelastic and annular dark field signals were detected simultaneously.

Nanogold Marking

Figure 1:
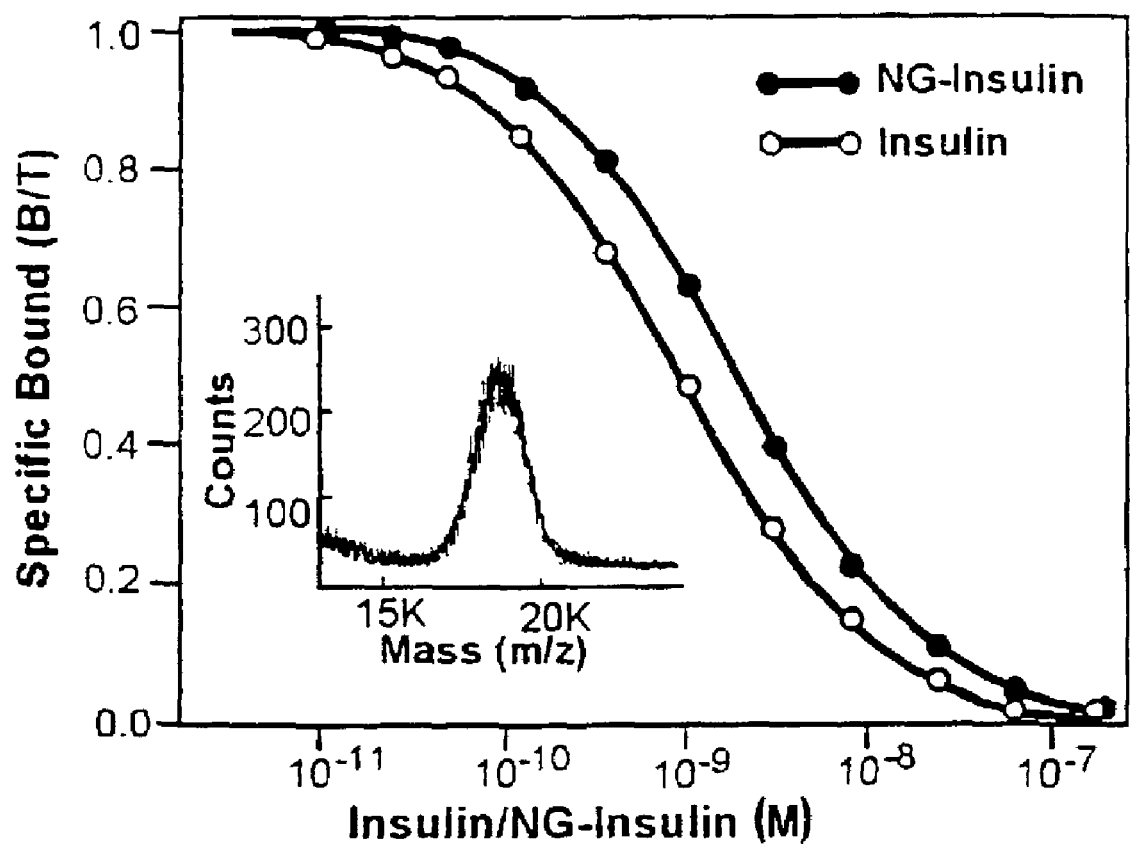
FIG. 1. Receptor-binding assay of Nanogold-insulin. Receptor-binding activity of purified Nanogold-insulin was compared to that of bovine insulin (SEQ ID NO:11 and SEQ ID NO:12) in a receptor-binding assay using human insulin receptor as described (9). Inset shows the mass spectrum obtained from the MOLDI-TOF analysis of purified Nanogold-insulin (7).
Figure 2:
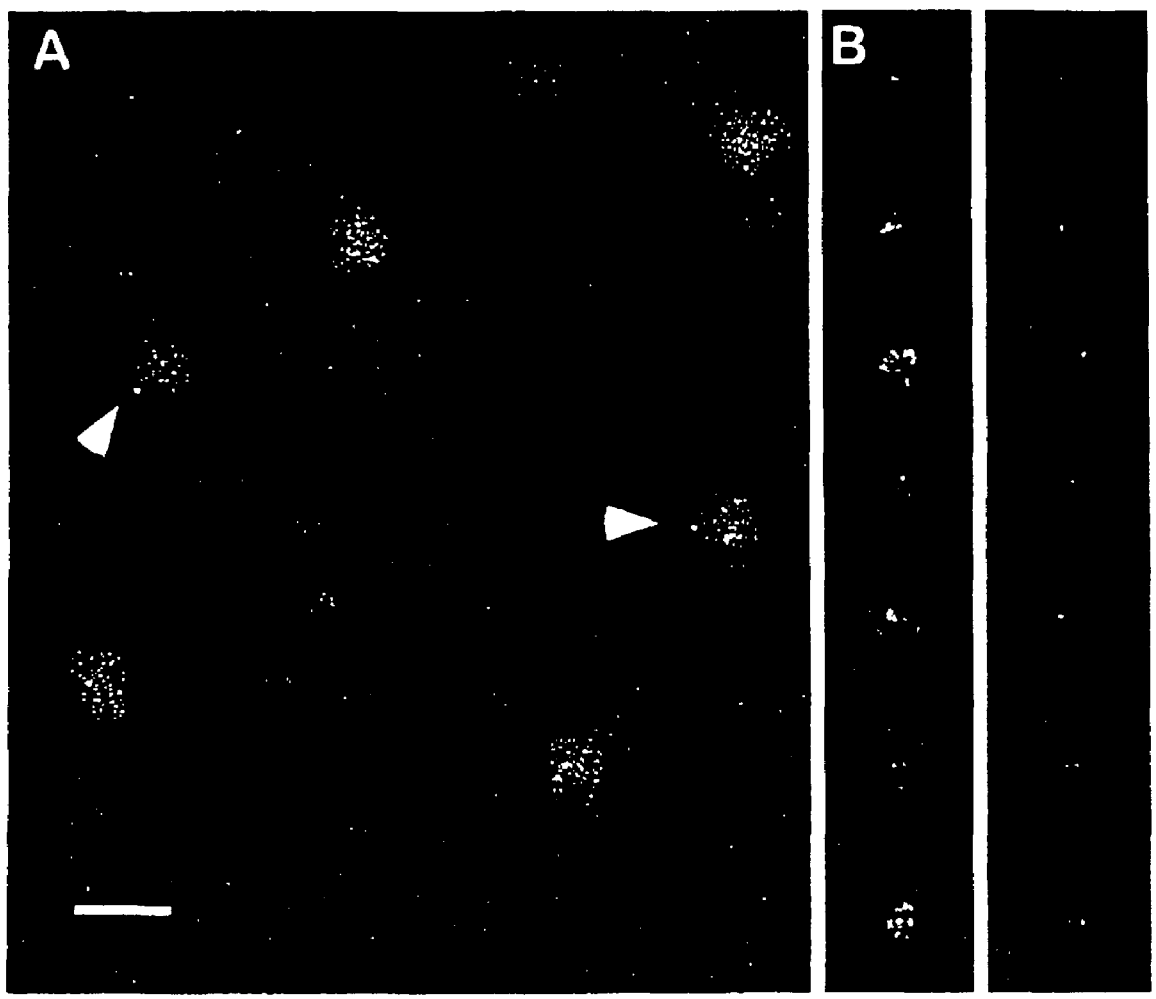
FIG. 2. STEM dark field images of human insulin receptor/Nanogold-insulin (HIR/NG-BI) complex. A) Raw images showing several complexes. Arrowheads point to intense signals from Nanogold marker. Scale bar=20 nm. B) HIR/NG-BI images extracted from image fields, after low pass filtering to 1.0 nm and boundary determination (left column). High density threshold representation of extracted images showing one (top five images) or two (bottom two images) sites of Nanogold location (right column).

The quaternary structure of IR bound to insulin was determined by marking with Nanogold. The 70 atom gold marker localized and delimited the insulin binding site. Compared to native bovine insulin, Nanogold-bovine-insulin (NG-BI), derivatized at the B-chain Phe1 ($^i$), a location not directly involved in receptor binding ($^{ii}$), bound to human insulin receptor (HIR) (SEQ ID NO:15, SEQ ID NO:16 and SEQ ID NO:17) with only a slightly reduced affinity (FIG. 1). Purified solubilized HIR (SEQ ID NO:15, SEQ ID NO:16 and SEQ ID NO:17) used in this study has been shown to be fully active ([iii]). Such HIR (SEQ ID NO:15, SEQ ID NO:16 and SEQ ID NO:17), incubated with NG-BI to form the HIR/NG-BI complex in the absence of ATP, was subjected to low-dose dark field STEM imaging at −150° C. FIG. 2A shows a representative field of individual molecules. On average, each HIR/NG-BI complex measured 15 nm across. Based on its strong scattering, the 1.4 nm gold ligand of NG-BI was located on the image directly as a clear site of highest density, or could be demonstrated as such by thresholding. FIG. 2B shows examples of molecules with 1 or 2 sites of highest density, indicative of binding of one or occasionally two NG-BI particles, consistent with the known binding of between one and two insulins per IR (3). When two NG-BI particles were detected, they were in close proximity to each other.

Image Reconstruction

Figure 3:
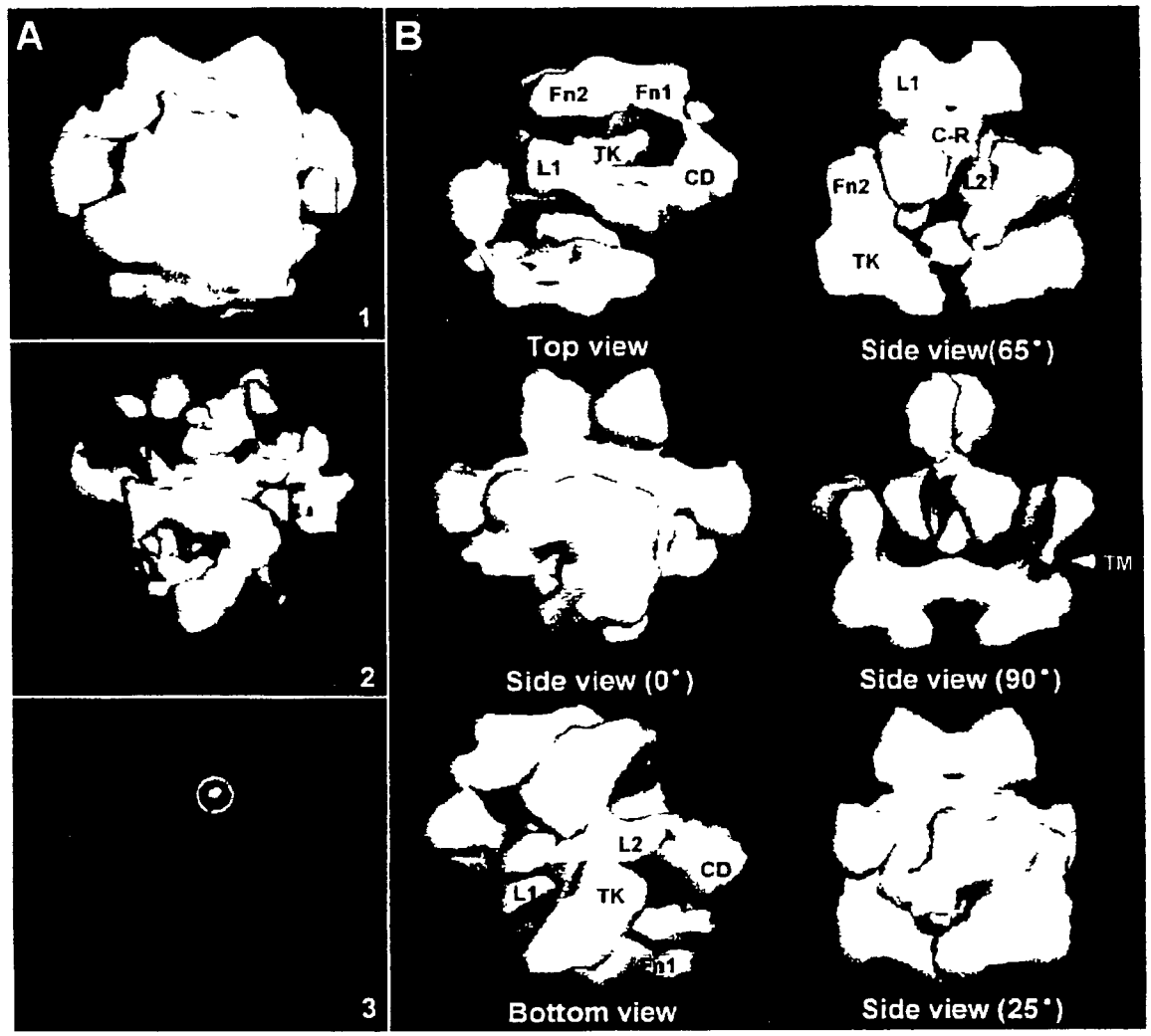
FIG. 3. Three-dimensional reconstruction of the HIR/NG-BI complex from 704 STEM dark field images. A) Density threshold representing the total expected volume for the complex [1]; intermediate density threshold, unsymmetrized, showing higher contiguous densities [2]; high density threshold of [2] showing only the Nanogold label [3]. Circles in the panels indicate location of the gold marker within the reconstructions. The resolution was 20 Å as measured by Fourier phase residual analysis of two reconstructions with 352 images each (13). B) Reconstruction with two-fold symmetry at intermediate density thresholds in different orientations, indicating the relationship and connectivity of the structural domains. Labels, for only one $\alpha\beta$ monomer of the dimeric HIR, refer to biochemical domains. Arrowhead indicates the proposed plane of the cell membrane lipid bilayer. L1, C—R, L2=L1-Cysteine-rich-L2 domains; CD=connecting domain; Fn1, Fn2=fibronectin III repeats 1 and 2; TK=tyrosine kinase; TM=transmembrane domain.
Figure 4:
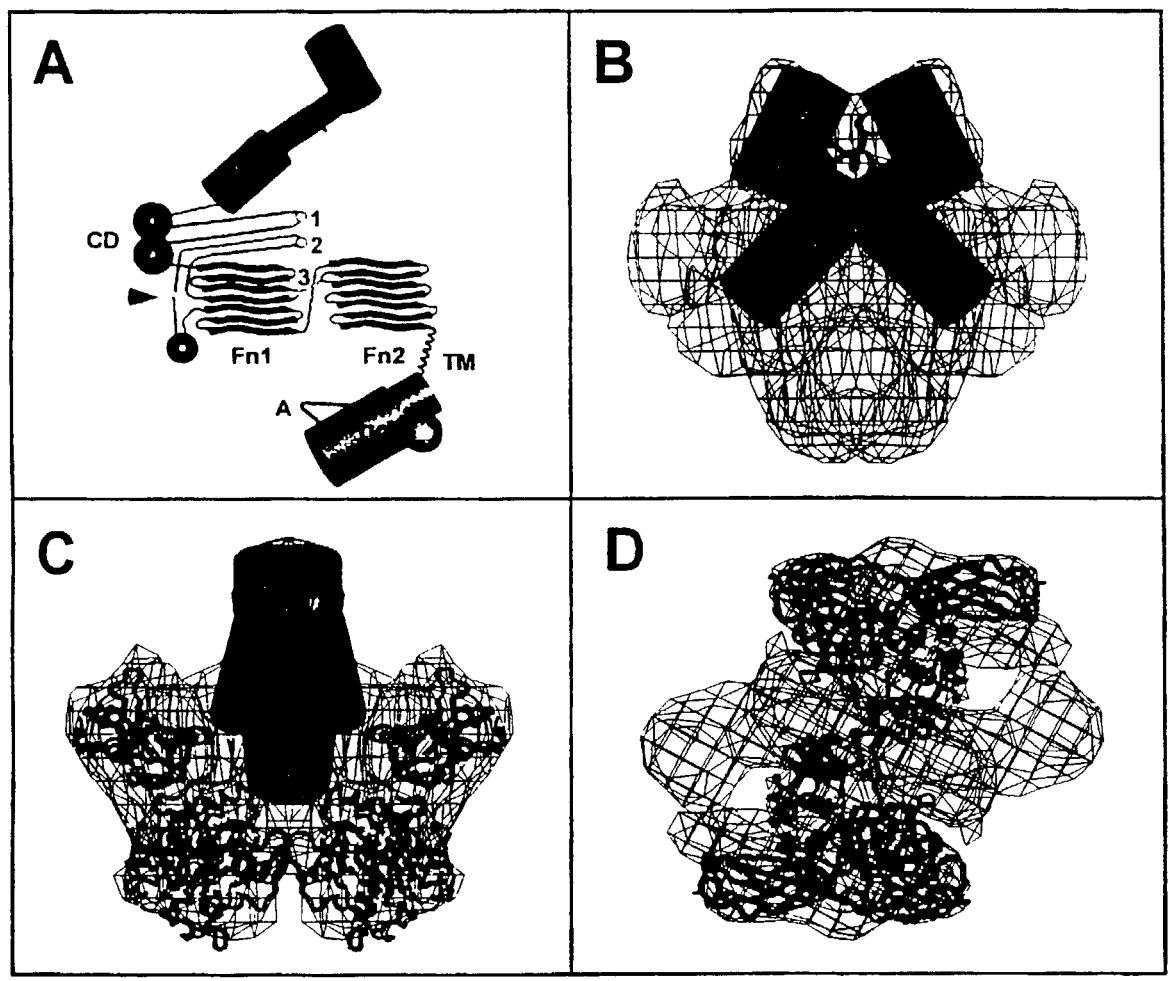
FIG. 4. Fitting of biochemical domains and their known x-ray structures to the 3D reconstruction. A) Schematic domain structure for one $\alpha\beta$ monomer, derived from i) connectivity of the 3D reconstruction at intermediate density threshold (FIG. 3), ii) from the primary domain sequence, iii) from the requirement for two disulfides on the two-fold symmetry axis between the two $\alpha$ subunits (4), iv) the fit of the known domain structures, and v) the principle of keeping domains of unknown structure as compact as possible. Distances measured in the 3D reconstruction between locations of subdomains CD, Fn1 and the symmetrical disulfides were commensurate with numbers of intervening amino acid residues (structures not shown to scale; unknown structures are spheres or lines): A=TK activation loop; 1=Cys524; 2=Cys682, 683, 685; 3=alpha-beta disulfide between Cys647 and Cys872; arrowhead=proreceptor cleavage site; other labels as described in FIG. 3B. B) Representative fitting of L1-Cys-rich-L2 domains as approximate cylinders to ectodomain structure of 3D reconstruction (cf.

Approximately 700 images were selected for reconstruction on the basis of having a definite site of high density, the expected mass for the complex, being structurally contiguous, and being separated from neighbouring images. The 3D reconstructions of the HIRING-BI complex are shown in FIG. 3. The interpreted alignment and the fit of the biochemical domains to this structure are detailed in FIG. 4. The 3D structure at the full expected volume is compact and globular (FIG. 3A, top panel). The NG-BI particle was located on the 3D reconstruction by increasing the density threshold without imposing symmetry (FIG. 3A, panel 2 and 3), to pinpoint the binding site and to limit the fit of insulin to its vicinity within the IR complex. Since insulin binds to the L1-Cys-rich-L2 regions of the ectodomain of IR, the NG cluster identifies this region of IR in the reconstruction.

Paired elastic and inelastic images were combined to increase the signal-to-noise ratio two-fold. Single particles were interactively selected in 64×64 pixel windows using the program WEB (Wadsworth Laboratories, Albany N.Y.), and low-pass filtered to 1.0 nm using a Gaussian filter in the program SPIDER (Wadsworth Laboratories, Albany N.Y.). The molecular mass was calculated relative to the 23 Å carbon support with a density of 2.0 g/cm$^3$. The particles had a Gaussian mass distribution with a modal mass of 570 kDa, which includes the mass of 480 kDa for the HIR and NG-BI plus the weight for an estimated 150 Triton X-100 molecules. Particle images were "grown" from a central high density in expanding contiguous contour levels to a global cut-off corresponding to the average mass. Relative orientations were computed as before (N. A. Farrow and F. P. Ottensmeyer, *J. Opt. Soc. Am.* A9, 1749 (1992); N. A. Farrow and F. P. Ottensmeyer, *Ultramicroscopy* 52, 141 (1993); G. J. Czarnota, D. W. Andrews, N. A. Farrow, F. P. Ottensmeyer, *J. Structural Biology* 113, 35 (1994); G. J. Czarnota, D. P. Bazett-Jones, E. Mendez, V. G. Allfrey, F. P. Ottensmeyer, *Micron* 28, 419 (1997)) and 3D reconstructions were performed by filtered back-projection using an angular distribution-dependent filter. Measurements of resolution were obtained via Fourier shell phase residual calculations between reconstructions of two independent sets of half of the 704 images each (G. J. Czarnota, D. W. Andrews, N. A. Farrow, F. P. Ottensmeyer, *J. Struct. Biol.* 113, 35 (1994)). Calculations were carried out on an SGI Indigo workstation (Silicon Graphics Inc., Mountain View, Calif.). The program IRIS EXPLORER 2.0 (SGI, Mountain View, Calif.) displayed the 3D reconstructions. To show domain relationships and structural links, the reconstructions were displayed with intermediate densities between 5% and 10% higher than the average density for the full volume. INSIGHT II (Molecular Simulations Inc., San Diego, Calif.) was used to dock known crystal structures and approximate models. Handedness of the construct was determined by fitting the x-ray crystallographic structure of tyrosine kinase domain into mirror pairs of the 3D reconstruction.

EXAMPLE 2

Structural Characteristics of IR

Domain-like features of the structure become evident at intermediate density thresholds (FIG. 3A, panel 2), and, except for the NG-BI region, these indicate a strong 2-fold vertical rotational symmetry as anticipated from the dimeric configuration of the oligotetrameric $(\alpha\beta)_2$ structure of IR. This symmetry was used to reduce noise in the reconstructions and render the structures shown in panel 1 and in FIG. 3B, as being viewed in the plane of the membrane, and in the extracellular (top) and intracellular (bottom) perspectives. Views of these structures are reminiscent of the X- and Y-shaped electron microscopic images previously observed for IR or its ectodomain.

In the side views, the top part of the structure, where NG is located, is identified as the ectodomain of the α subunit (SEQ ID NO:16). The dog-bone-shaped substructure of the 3D reconstruction, (FIG. 3B, top view), and equivalently the top-most, bow-tie-shaped structure (FIG. 3B, 0°), are designated as the two L1 domains of the dimeric receptor on the basis of the x-ray structure of the L1-Cys-rich-L2 domains. The side view at 65° shows the L1-Cys-rich-L2 domains as contiguous substructures across the upper central region of the molecule, with enough additional volume in this region to account for most of the remaining mass of the two α subunits, primarily the connecting domains (CD).

The contiguity of the domain structure (FIG. 3B, top and side view 90°, along with the primary domain sequence (FIG. 4A), shows that the two β subunits (SEQ ID NO:17) occupy the lower half of the structure, distal from L1, reaching up and out as a contiguous mass. The intracellular TK domain of IR would then occupy the bottom portion of this structure with two IR fibronectin type III (FnIII) repeats in each receptor half being in the top portion of the crescent-shaped spiral of the β subunit (SEQ ID NO:17) at the same level as the L2 domain in the α subunit (SEQ ID NO:16). One of the FnIII repeats, composed of residues from both the α (SEQ ID NO:16) and β subunit (SEQ ID NO:17), is assigned to the upper left end of the crescent (side view, 0°) where it is contiguous with the CD portion of the α subunit (SEQ ID NO:16) (top view). FIGS. 4C and 4D (cf. FIG. 3B, 90°, top view, respectively) show the fitting of the crystal structure of the TK domain of the β subunit (SEQ ID NO:17) and of the two FnIII repeats modelled as the canonical fibronectin type III structures (16).

The masses of the kinase domains are connected via a slender horizontal bridge (FIG. 3B, side view 90°) that was not observed in the x-ray structures of the TKs, but can be explained in terms of the reconstruction being in a transition between free IR and its ligand-activated form. In the two symmetrically fitted TK (FIGS. 4C and 4D) crystal structures the catalytic loops are separated by 4 nm. This distance is just sufficient to permit the tyrosine triplet (Tyr1158, 1162 and 1163) in a fully extended flexible activation loop of one TK to reach the catalytic loop of the opposite TK as modelled from the x-ray coordinates (PDB 1IRp). The extension of the activation loops, equivalent in cross-section to four extended polypeptide chains, easily accounts for the linking density observed between the lower portions of the β subunits (SEQ ID NO:17) (FIG. 3B, 90°). This is an important difference from the x-ray structures of the inactive and activated TKs as discussed below.

The spatial relationship between the domains of the α (SEQ ID NO:16) and β (SEQ ID NO:17) subunits (e.g. side view, 90°) shows the location of the cell membrane lipid bilayer as the space below the α subunits (SEQ ID NO:16) and above the bridge linking the two assigned TK domains. Instead of a flat open region, this space in the 3D reconstruction forms a thick dome-like slab above the bridge with a thickness variation of 2.2 to 2.7 nm. This spacing is a change in shape from, and a decrease in the thickness expected for a membrane bilayer that would accommodate an alpha-helical transmembrane domain (TM) of 23–26 hydrophobic amino acids. However, since the purified IR in the absence of its native membrane was fully active, the relative positions of the extracellular and intracellular domains must still represent a close to native arrangement.

The crossing L1-Cys-rich-L2 domains of the dimeric α subunits (SEQ ID NO:16 were presented (FIGS. 4B and 4C). We determined the x-ray coordinates with IR from the domain structures (5) (See FIG. 7). Using this structure, the localization of the gold cluster, and the known receptor-binding domain of insulin (8), we have fitted an NG-BI molecule into this region. The best fit is obtained with a molecule of insulin, partially on the two-fold symmetry axis of the dimer, being in contact with the L1-Cys-rich domains of one α subunit (SEQ ID NO:16) and with the L2 domain of the other α subunit (SEQ ID NO:16). A model involving both α subunits (SEQ ID NO:16) in the high-affinity binding of insulin has previously been proposed based on studies of insulin analogues binding to IR and IR/IGF-I R chimeras ($^{iv}$). Our 3D reconstruction shows this involvement. Although two molecules of insulin can be fitted to this configuration, two molecules of Nanogold-labeled insulin were observed only rarely in the STEM images. The high-affinity binding of the first insulin molecule to the IR has induced a conformational change in the binding domain so that the second insulin molecule would bind only at low affinity. Likewise the binding of a second molecule of insulin could effect a conformational change that enhances the dissociation of the bound insulin. Thus the curvilinear Scatchard plot and the negative cooperativity of insulin binding ($^v$) can be explained on the basis of the 3D reconstruction. The reconstruction also explains why only low-affinity binding is obtained with purified αβ monomer.

Superimposition of known crystal structures of smaller domains of the receptor on substructures of the 3D reconstruction has made it possible to deduce the spatial relationship among the domains in the complex. The structure shows the division of the complex into the extracellular and the cytoplasmic segments along a plane, the cell membrane, on which the fibronectin type III repeats lie (16–18). These repeats appear pontoon-like to support the centrally located insulin-binding segment of the ectodomain.

Monomeric inactive receptor TKs such as EGFR are brought together by ligand binding and become activated as dimers resulting in TK autophosphorylation. In the intrinsically dimeric IR-family receptors, the distance between the two cytoplasmic β-subunit TKs within the dimer must be too great without ligand binding for the activation of the kinase. Hubbard et al. (4) suggested that insulin binding to IR decreased this distance by disengaging Tyr1162 from the catalytic loop to enable trans phosphorylation in the presence of ATP. In our reconstruction a good fit to the ligand-receptor complex is obtained when the two TK domains are oriented with their catalytic loops juxtaposed. In this orientation the extended flexible activation loop of each TK, which moves 30 Å between the inactive and activated states in the crystal structures (4), can just reach the catalytic loop of the opposing TK to be activated. These two loops can easily form the linking mass density between the TKs seen in the 3D reconstruction in the absence of ATP.

The 3D structure obtained from images of the HIR complex containing only a single NG-BI, shows that one molecule of insulin is sufficient to bring the two αβ monomers to an activating configuration. The dimeric receptor with a Ser323Leu mutation in the L2 domain of both α subunits (SEQ ID NO:16) showed a severe impairment in insulin binding, whereas a hybrid receptor with only one of the two α subunits (SEQ ID NO:16) mutated was found to bind insulin with high affinity and was fully active as a tyrosine kinase. Based on our 3D reconstruction, insulin bound to the L1 domain of the mutant α subunit (SEQ ID NO:16) and the wild-type L2 domain of the hybrid IR and the binding of only a single molecule of insulin is sufficient for TK activation.

Thus we have obtained the 3D quaternary structure of the IR-insulin complex formed in the absence of ATP. The structure was an intermediate between insulin-free IR and the fully activated, phosphorylated IR. The reconstruction is readily interpreted as such: as a receptor poised for activation by trans-phosphorylation. We determine the full extent of conformational changes induced by insulin binding. We reconstruct the initial state of free IR and the final activated state for comparison. The 3D reconstruction presented here provides concrete structural information towards the full understanding of transmembrane signal transmission in insulin action. Furthermore, the approach used in this study can be applied to obtain the quaternary structure of other membrane proteins or receptors that are refractory to crystallization. The invention includes the methods for studying polypeptide structure described in this application.

EXAMPLE 3

Mechanics of Transmembrane Signalling of the Insulin Receptor

The binding of insulin to the extracellular domain of the insulin receptor (IR) begins an intracellular signal cascade that ends in numerous insulin-specific cellular responses. The binding event activates the intracellular tyrosine kinase (TK) domain of the receptor. How the signal is transmitted across the cell membrane has remained a mechanistic puzzle, since complete membrane receptors have been refractory to high resolution structural studies by NMR spectroscopy or by crystallography. In an alternative approach we have used low-dose low-temperature dark field scanning transmission electron microscopy (STEM) to determine the three-dimensional quaternary structure of the entire isolated 480 kDa human insulin receptor bound to insulin[1]. Recently the atomic co-ordinates of individual N-terminal domains of the extracellular region of a highly homologous receptor, the insulin-like growth factor type 1 receptor (IGF-R) have become available, as have models of the three individual fibronectin type III (Fn) domains of IR[10,31]. We have modified these domain structures substituting the IR amino acid sequence and accommodating the covalent dimeric character of IR. The IR TK domain structures were available previously[8,9]. All of these domains were fitted into the quaternary structure calculated from STEM micrographs. The fit provides a detailed description of the insulin binding site of IR and of its interactions with insulin. Moreover, the entire 3D complex is a molecular machine with intrinsic linkages that provides a mechanistic model for transmembrane signal transduction by IR. Since IR is constitutively dimeric[2], the mechanism of IR signal transduction is of necessity different from that of many receptors activated by ligand-induced dimerization. Instead, the binding of insulin changes the IR dimer from a configuration that inhibits TK activation to one that is openly permissive of TK transphosphorylation.

The structure and model explain observations on insulin binding, on disulphide modifications linking the two monomers and linking their constituent domains, the block to TK activation, dominant negative mutations, insulin-dependent and insulin-independent autophosphorylation, and transmembrane modifications. Moreover, the model is sufficiently general to serve as an archetype for dimeric two-state receptors like IR that are activated or inhibited by ligand binding.

Figure 5:
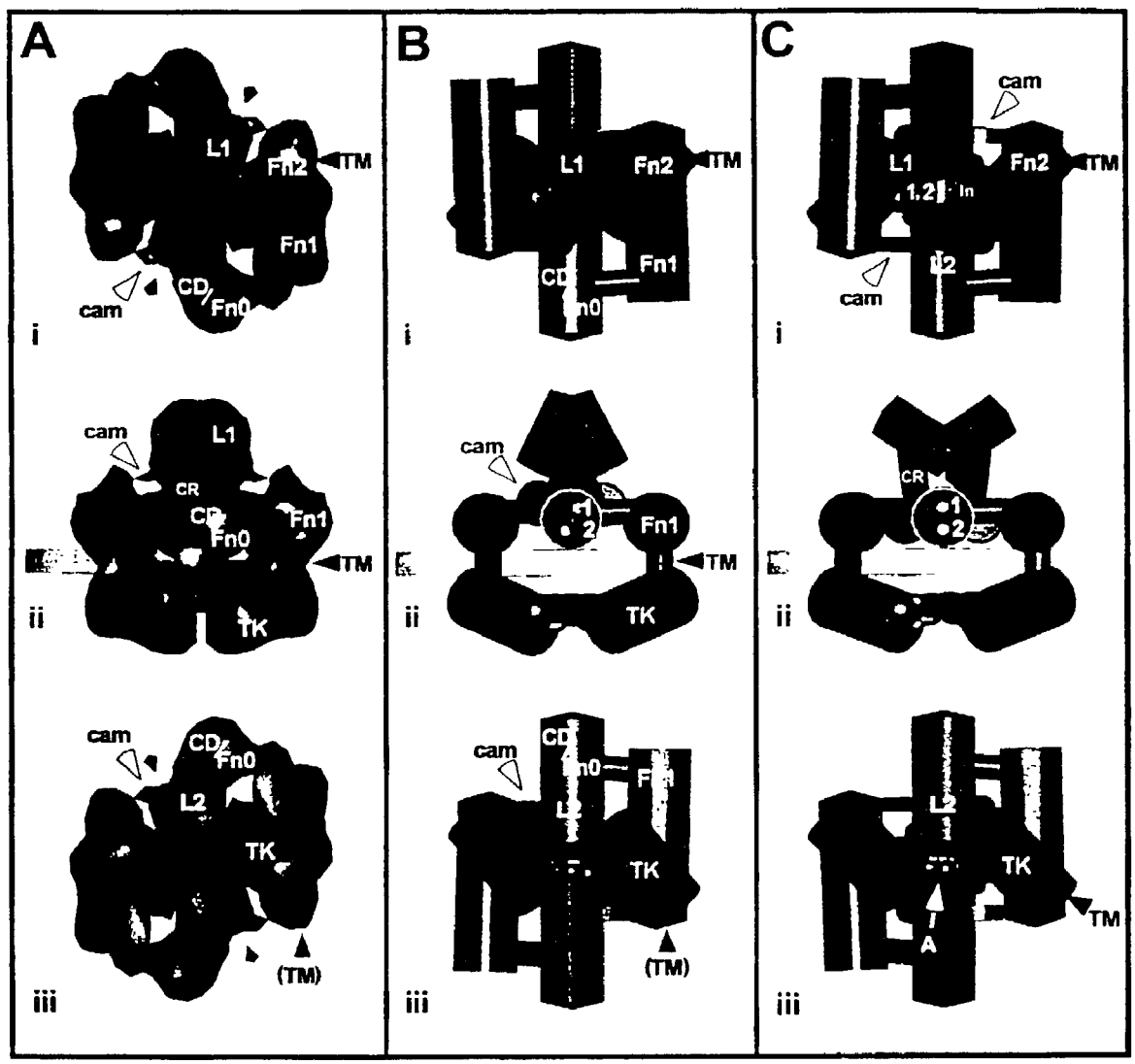

The 3D structure determined at 20 Å by reconstruction from electron micrographs of sets of single insulin-bound IR complexes[1] is shown in FIG. 5, with views as seen from the exterior of the cell membrane (FIG. 5a(i)), the interior of the cell (FIG. 5a(iii)), and at 90° from these in the plane of the membrane (FIG. 5a(ii)). Antibody labelling has recently confirmed the location of three pairs of the assigned ectodomain regions[3].

Covalent linking of the two monomers of IR occurs between Cys524 of each monomer, and also between corresponding Cys682 (or 683 or 685) moieties[4-7]. Each monomer itself contains a 135 kDa α subunit (SEQ ID NO:16) and a 95 kDa β subunit (SEQ ID NO:17) linked by a single disulphide bond (αCys647 to βCys872)[4]. The structure of one monomer is diagrammed in FIG. 6. From considerations of symmetry of the $(\alpha\beta)_2$ dimer, the two α—α disulphide bonds[5,7] occur one above the other on the two-fold symmetry axis of the dimer (labelled 1 and 2, FIG. 6). In the interpretation of the 3D structure, two polypeptide chains link the β subunit from fibronectin domain Fn1 to the connecting domain CD/Fn0 and insert domain ID of the central α subunit.

Crystal structures were determined only for parts of IR: the intracellular TK domain in the unphosphorylated state as well as phosphorylated and bound to a peptide substrate[8,9], and the first three extracellular domains, L1, Cys-rich, and L2, of the homologous type 1 insulin-like growth factor receptor (IGF-1R)[10]. From analysis of sequence homology each αβ monomer contains three fibronectin type III repeats[11,13,31]. The ID of the α subunit (SEQ ID NO:16), the transmembrane and juxtamembrane regions and the ID and C-terminal domains of the β subunit (SEQ ID NO:17) are still of unknown structure.

EXAMPLE 4

Docking of L1-CR-L2

The atomic co-ordinates of the L1-CR-L2 regions of IGF-1R (PDB: 1IGR) were used to substitute and insert corresponding amino acids for IR into the IGF-1R structure. Additional loops that do not exist in IGF-1R, e.g. amino acids 272–275, were inserted where necessary. This was followed by several rounds of molecular dynamic calculations using the program InsightII (Molecular Simulations, San Diego, Calif.) to eliminate atomic clashes and to approach a corresponding energy minimum for the IR sequence. No rotations of the L1, CR, or L2 domains relative to each other were carried out during any of the procedures. Two IR-based L1-CR-L2 structures, one for each IR monomer, were then docked symmetrically into the central ectodomain of the quaternary IR dimer structure according to the domain sequence scheme proposed previously[1]. Several other symmetric configurations were tested as well, such as reversing the positions for L1 and L2 or rotating the L1-CR-L2 structure to extend L2 into the regions designated for the CD/Fn0 domains. The final fit maximized overlap of the EM-based mass with the atomic structure, while avoiding overlap of the atoms of the two L1-CR-L2 cross-over regions (FIG. 7a). Moreover, this configuration resulted in an additional fit of loops in the L1 regions to slender masses extending from the corresponding regions of the EM structure (FIG. 7b) and provided atomic confirmation for the cam-like structures on the CR regions (FIG. 7c). These cam-like structures are formed by a loop of amino acids from 250 to 280 that is stabilized by a disulphide bond between Cys266 and Cys274[32].

EXAMPLE 5

Insulin Binding Region

The fit of the two L1-CR-L2 regions formed a diamond-shaped central tunnel (FIG. 7a). Each CR domain and the juxtaposing L2 surface of the opposite monomer formed one side of the diamond, proximal to the membrane. The other two sides were formed, one each, by the L2-facing surface of L1[10]. This arrangement lined the tunnel with almost all of the amino acids that are linked to the binding of insulin. The atomic structure of human insulin (PDB:1BEN) fitted into this tunnel as shown in the stereo view in FIG. 8a, involving binding sites on both monomers. Insulin interaction with one monomer involved major hydrophobic areas on the insulin B chain (ValB12, TyrB16, LeuB17, and PheB24 to TyrB26) and on L1 (Leu87 to Phe89, and Tyr91), as well as interactions between GluB21 on insulin and His247 and Gln249 of the CR region (FIG. 8b). Interaction with the other monomer was predominantly electrostatic with no obvious hydrophobic components (FIG. 8c). These interactions and others are given in Table 1, as are some of the distances between interacting side chains.

One overriding constraint on the docking of insulin was the need to satisfy the location of the Nanogold label attached to PheB1 of insulin for electron microscopy[1]. This requirement was easily satisfied by flexing the insulin B chain between aminoacids 1 to 6, a motion that appears to occur naturally, as judged by the position of the B chain in different crystal structures of the molecule[34]. The fit indicated that the gold marker location was closest to L1 of the monomer interacting electrostatically with insulin (FIGS. 8a and 8c).

EXAMPLE 6

Fibronectin Linkers

Figure 6:
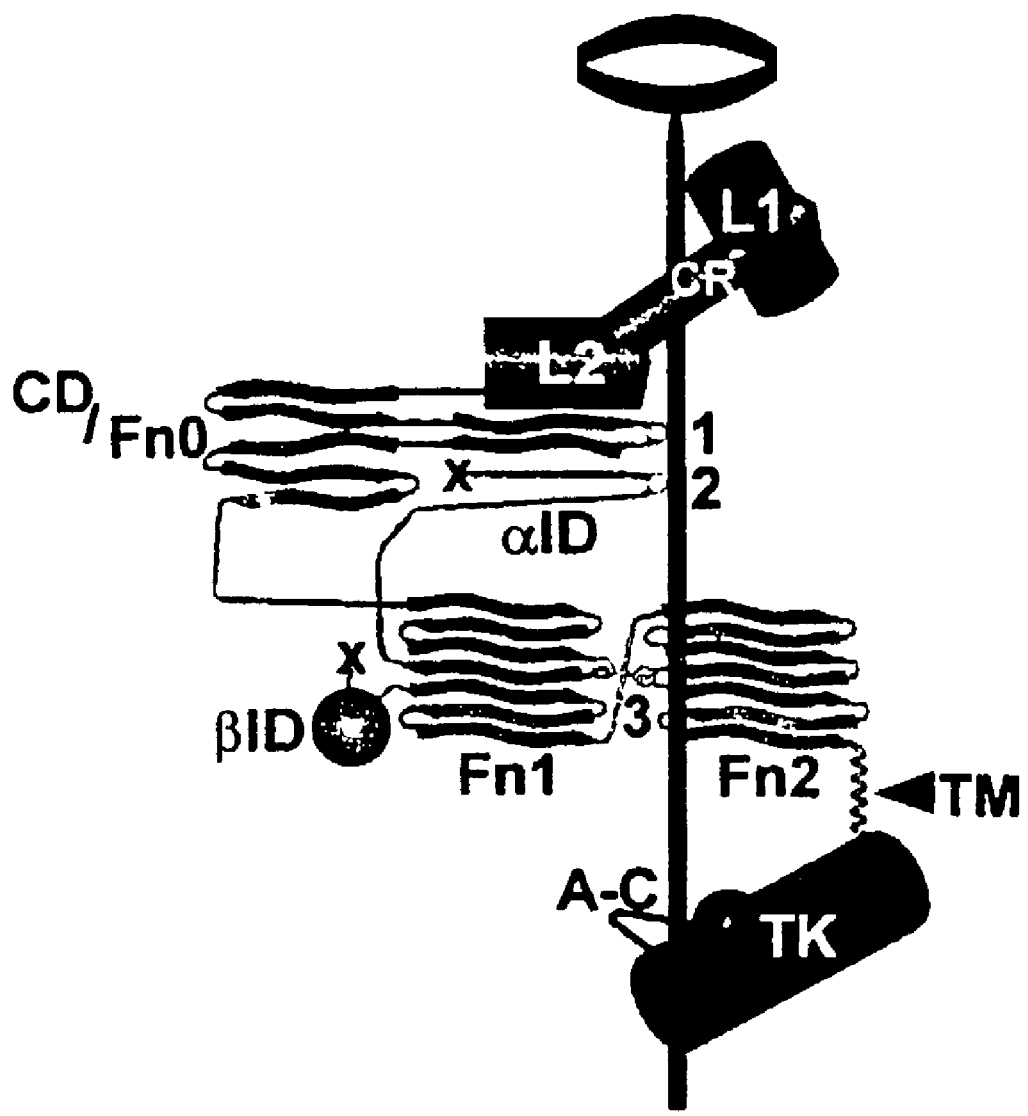

The linkage in the ectodomain between the L1-CR-L2 regions and the IR transmembrane domain is via three fibronectin type III (Fn) domains and two so-called insert domains, one each on the α (SEQ ID NO:16) and β (SEQ ID NO:17) subunits of each monomer. This region also provides the two disulphide bonds that covalently link the αβ monomers to form the constitutive IR dimer. One disulphide bond occurs between the Fn0 domains of the α subunits (SEQ ID NO:16), the other between corresponding α insert domains (FIG. 6). Two of the Fn domains, Fn1 and Fn2 are not involved in dimer formation, and have been modelled into the 3D reconstruction previously as the normal seven-beta-strand fibronectin type III structure[1], even though Fn1 is made up of four beta strands from the α subunits (SEQ ID NO:16) and three from the β subunit[6] (SEQ ID NO:17).

In relation to our quaternary IR dimer structure, the α insert domain is modelled to lead out of the Fn1 domain across to the CD/Fn0 region, and then to lie against the near side of the L2 domain until it reaches the diad axis of the dimer. Here it forms a disulphide bond with its symmetric partner insert domain. The location of the remaining 34 amino acids of this domain is unknown, although the final 12 residues appear to assist in insulin binding[2]. This shows that the peptide chain either remains near the central region or returns to the centrally located binding site.

The structure of the most N-terminal Fn domain, Fn0, designated CD in prior descriptions[11,31], is more problematical. The domain sequence of the quaternary structure shows that Fn0 is located at the extreme ends of the central region of the IR ectodomain[1]. The same conclusion is reached from the location and accessibility of monoclonal antibodies and Fab fragments against this region[3,33]. At the same time, the location of the α—α disulphide bond at Cys524 within this region requires that this domain extend to the diad symmetry axis of the IR dimer. To accommodate both requirements, the Fn0 domains were placed at the ends of the central ectodomain. However, a hairpin structure, containing the Cys524 loop and two neighbouring beta strands of the seven-stranded Fn configuration, was unfolded from the Fn beta sandwich and layed against the contiguous L2 domain on the side opposite the insert domain loop placement above. This manoeuver permitted the Cys524 residue to reach the diad axis and form the second α—α disulphide bond. In addition, Fn-like configuration of this domain still easily accommodated the internal linkage to the C-terminal of L2, provided an exposed location of the monoclonal epitope between residues 535 and 548[31,33], and retained the normal location of the Fn0 C-terminal, suitably positioned for the flexible linkage leading into Fn1 (FIG. 6). Moreover, the additional size of this Fn region (122 amino acids versus 106 and 97 for Fn1 and Fn2, respectively) provided enough mass to accommodate the volume of this region in the EM reconstruction.

EXAMPLE 7

Physical Model for Transmembrane Signalling

In contrast to activation of monomer membrane receptors, activation of the IR tyrosine kinase cannot be caused by ligand-induced dimerization, since IR is intrinsically dimeric. However, the articulated structural features of the IR dimer indicate obvious mechanical arrangement that permits transmembrane signalling and intracellular recognition both of the absence of insulin on the receptor and of insulin binding to it.

FIG. 5a shows that the central, extracellular region of the two sets of contiguous domains from L1 to Fn0 is flanked on both sides by the pontoon-like Fn1/Fn2 domains, which are tethered asymmetrically only between Fn1 and Fn0. The two Fn2 ends, which terminated at the juxtamembrane and transmembrane (TM) domains, are held away from the central regions by the bumper-like cam structures of the two symmetry-related CR domains. The intracellular TK domains are then influenced by the TM and juxtamembrane domains to which they are attached.

Nuclear magnetic resonance studies have shown that helical TM domains, similar to the IR TM, cannot transmit a signal longitudinally along their lengths[37]. At most a torsional force can be exerted by them. However, they can shift laterally within the membrane. This provides a simple and direct means for transmembrane signalling for IR.

Figure 9:
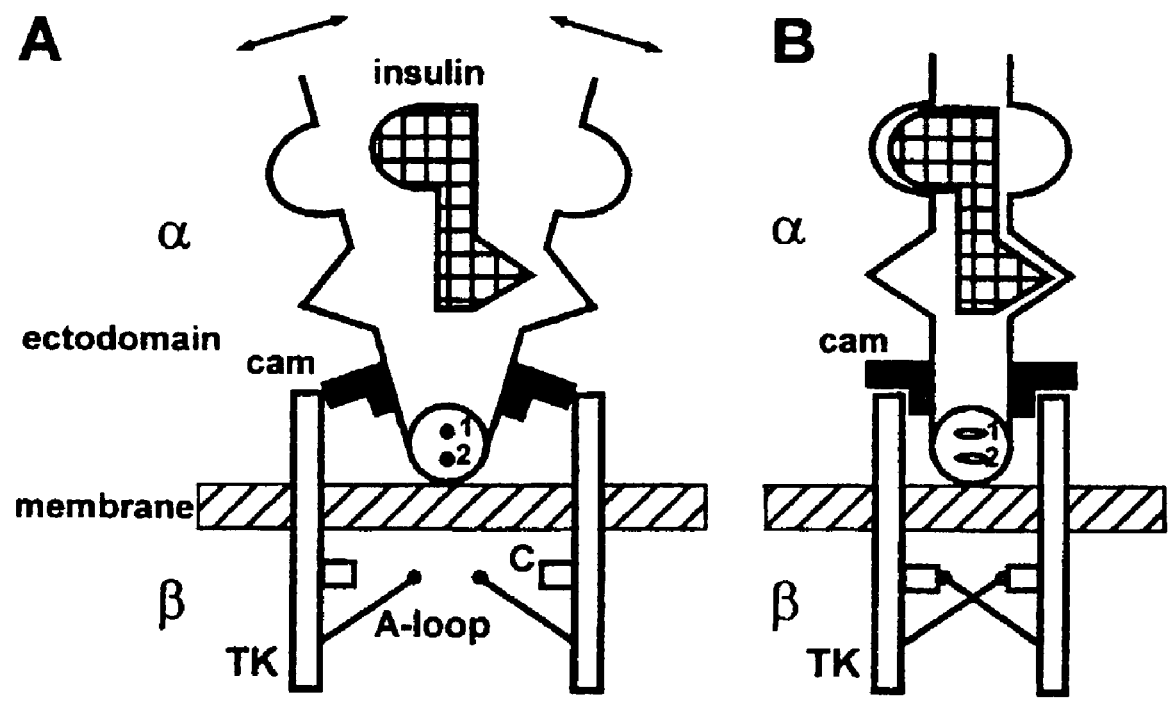
Figure 10:
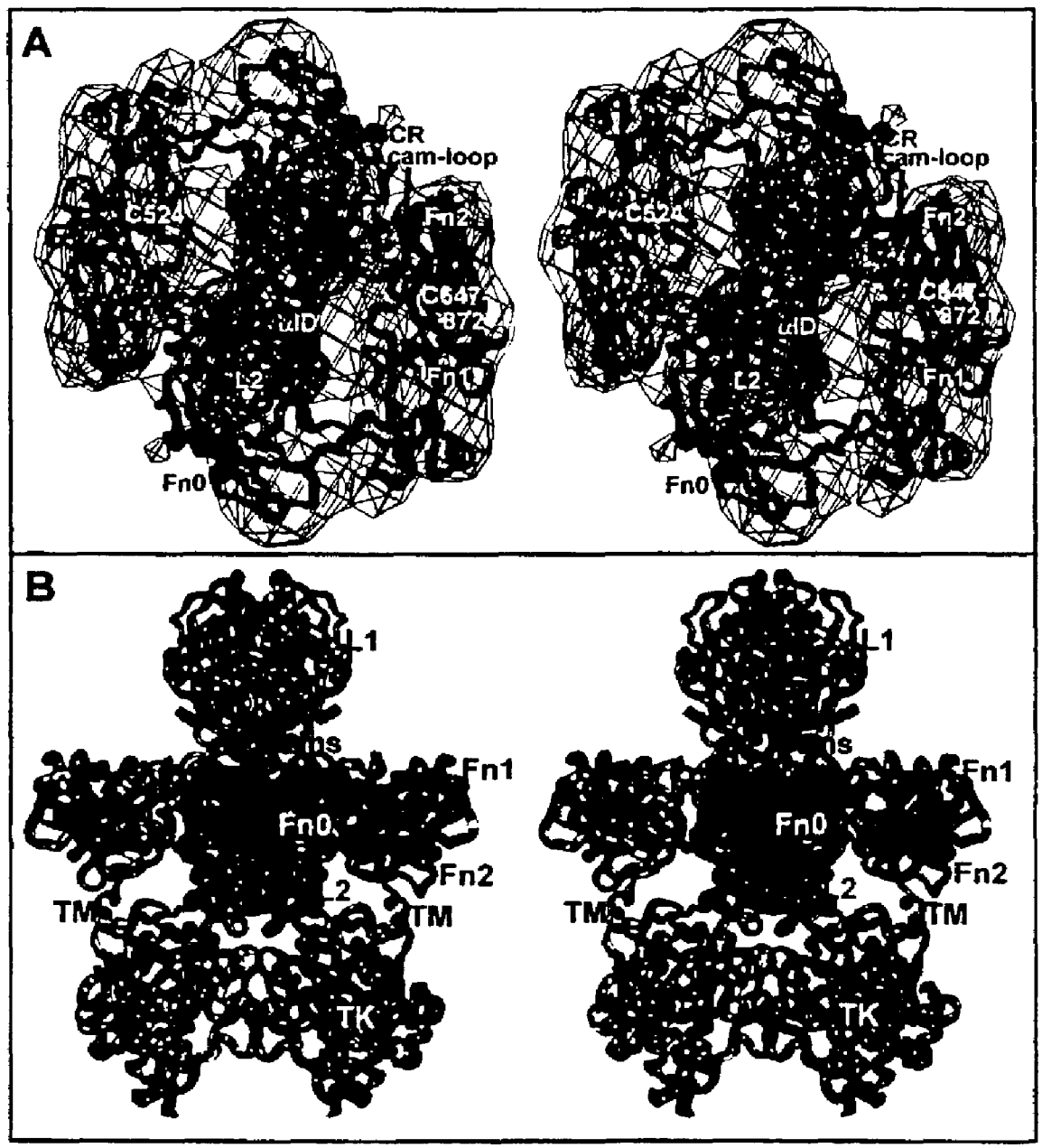

The structural basis for the proposed mechanism of IR transmembrane signal transduction is depicted in FIG. 9, pared to a two-dimensional representation. In the inactive state (FIG. 9a) the β subunit (SEQ ID NO:17) transmembrane regions and the associated intracellular TKs are held apart by the cam-like blocks on the central portion of the dimeric α ectodomain. The open extracellular structure of the IR dimer shows that the two sets of L1-CR regions are splayed apart. When a single insulin molecule with its two different binding regions[15] attaches to a contralateral pair of the four binding sites of the two α subunits[16] (SEQ ID NO:16), the bumper-like cam regions are rotated and lifted out of the way of the extracellular domains of the β subunits (FIG. 9b). The closed structure is based on the 3D reconstruction[1].

A more realistic depiction of the contiguous three-dimensional structural features of the IR dimer (FIG. 5a), that alternately permit and prevent TK activation, is the set of connected cylinders in FIGS. 5b and 5c. The perspective of FIGS. 5b(ii) and 5c(ii) is similar to FIG. 9. The insulin-binding domains, L1 and Cys-rich (CR), of each monomer (one blue, one fuchsia), cross symmetrically near the middle of the structure. They are attached to the L2, CD/Fn0 and ID domains, modelled as contiguous central barrel structures joined together on the two-fold symmetry axis via the two inter-monomer disulphides (labelled 1,2 in FIGS. 5b and 5c). The cam-like protrusions on the CR domains, represented as discs, abut the Fn2 domains of the β subunits (SEQ ID NO:17). These protrusions can just be seen in the high-density representation of the 3D reconstruction (cam, FIG. 5a). The mass of the cam reaches across from the centre to the Fn2 region in the full-volume representation (FIG. 7b). Near the CD/Fn0 ends of the barrels, each α subunit (SEQ ID NO:16) structure extends sideways to help form the Fn1 repeat and to tether each β subunit (SEQ ID NO:17) by a flexible joint to the central structure.

The N-terminal domain of the β subunit (SEQ ID NO:17) starts near the CD/Fn0 side arm of the α subunit (SEQ ID NO:16) (FIG. 6), leading into Fn1 and Fn2 of the extracellular domain of IR (FIGS. 5b and 5c). At that point the β subunit (SEQ ID NO:17) forms an axle-like transmembrane (TM) region[4], crossing the membrane before folding into the TK domain. Flexible activation loops (A) of both TKs[8,9] are modelled as extending towards the catalytic region of the opposite TK (FIG. 5c(iii)).

The insulin ligand, depicted as a disk, binds slightly asymmetrically with respect to the two-fold axis between the two αβ monomers[1], representative of the high affinity binding position (FIG. 5b). It is shown attached to only one monomer at the inception of binding to the open, insulin-free IR dimer (FIG. 5c).

EXAMPLE 8

Mechanism

In the inhibitory, insulin-free state (FIG. 5c), a minimum separation is maintained between the two intracellular TKs, in spite of thermal motion, by the α-ectodomain CR cam regions that contact the β-ectodomains at the Fn2/TM domains. Consequently, the distance between the intracellularly attached TKs prevents the flexible TK activation loop of one TK from reaching the catalytic transphosphorylation site of the other TK[8,9] (FIG. 5c(ii and iii), "A" arrow).

High affinity binding of a single insulin molecule joins the two L1-CR-L2 domains of the ectodomain (FIG. 5b) against a small torsional resistance offered by the two on-axis disulphide bonds (cf. FIG. 5b(ii) and FIG. 5c(ii)). This action rotates and lifts the cam protrusions, such that thermal motion can bring the pair of Fn2/TM-axle regions closer to the central barrel of the ectodomain. The reduction in separation between the TM axles permits a sufficiently close approach of the associated TK domains to allow transphosphorylation of the activation loop at the catalytic locus of the opposite TK (FIG. 5b(ii and iii)).

When insulin detaches from the receptor, the two L1-Cys-rich domains spring apart again, as the two strained Cys—Cys linkages return to their equilibrium positions (1 and 2, FIG. 5c(ii)). At the same time the CR-region cams again restrict the approach of the TK domains (FIG. 5c(ii and iii)), increasing their separation, possibly to facilitate downstream signalling actions.

EXAMPLE 9

Functional Consequences of the Model

The detailed model of insulin binding, the relative positioning of the known domain structures into the quaternary structure of the IR dimer, and the proposed mechanism for transmembrane signal transduction explain many observations on the behaviour of IR. A few examples are detailed here.

The Insulin Binding Site

The symmetric juxtaposition of the IR-adapted L1-CR-L2 domains in the structure concentrated virtually all of the known binding interactions to insulin into a tunnel-like space that readily accomodated the insulin ligand. Both hydrophobic and ionic interactions are accommodated involving L1, L2 and the CR region. A number of insulin interactions change in character as either insulin or IR is modified. These now have structural explanations. Experimentally, the interaction of insulin with the CR loop from 243 to 251 had indicated a strengthening of binding with the introduction of positively charged aminoacids into this region[16]. The fitting of insulin into the model binding site indicates an interaction of GluB21 of insulin with His247 and possibly Asn249 in the CR loop. The presence of the negatively charged Asp250 in this vicinity weakens this interaction. Thus the addition of a positive charge in the 243/251 loop would clearly enhance the binding of insulin by providing a potential salt bridge to the GluB21 residue, while the substitution of this His247Asp permits a new ionic interaction with ArgB22.

Experimentally, a mutation in Phe89 of the L1 domain reduces insulin binding[30]. As indicated in Table 1, Phe89 forms part of a hydrophobic region in the insulin binding tunnel, that is juxtaposed to a hydrophobic surface on insulin. Any decrease in this hydrophobic region would be expected to decrease the strength of insulin binding.

A mutation of HisB10 in insulin to AspB10 creates a superactive insulin[35]. In the fit to the model HisB10 interacts with Arg14 of L1. A stronger ionic interaction would be expected to result with the introduction of asparagine in insulin at position B10.

Modification of IR on Insulin Binding

High affinity binding of insulin is initially augmented, then diminished, by reduction of the disulphides of IR with increasing concentrations of dithiothreotol (DTT)[17]. In the model, normal high affinity insulin binding must overcome an energy barrier created by the binding-induced elastic strain in the two α—α disulphide bonds on the diad axis of the IR dimer, due to rotation of the two L1-CR-L2 regions to the closed position. Reduction of one of the two disulphide bonds eliminates this torsional strain, removing the energy barrier, and facilitating high affinity binding. Further reduction separates IR into monomers, abrogating high affinity binding, which involves two α subunits in close proximity[17]. A similar effect would be expected for a deletion that includes one of the α—α disulphide bonds[18].

Autophosphorylation

Basal insulin-independent autophosphorylation of IR occurs naturally at a low level. In the model the low levels of autophosphorylation reflect the torsional resistance of the two on-axis disulphide bonds which control the position of blocking cams in the insulin-free equilibrium position (FIG. 5c). However, random thermally induced motion is occasionally sufficient to rotate the blocking CR cams momentarily to the permissive positions. If random motion simultaneously brings the TM regions with their associated TK domains close enough together, then a round of transphosphorylation can occur even in the absence of insulin. Experimentally, such autophosphorylation is stimulated by mild reduction with DTT, then drops off to zero at higher DTT concentrations[17]. The breakage of either of the disulphide bonds would remove the resistance to random rotation to the permissive position, resulting in a more frequent random approach of the TK domains for transphosphorylation. The reduction of both bonds would result in monomeric IR, halting transphosphorylation altogether.

Deletional Activation

The IR is activated artificially by removal of amino acids 1 to 578 through tryptic digestion[19]. This cleavage still retains covalent links between the monomers and between the alpha (SEQ ID NO:16) and beta (SEQ ID NO:17) subunits. However, the insulin-binding region and the CR domains have been removed, along with their physical "cam structures". Thus the β domains and their TKs can move closer together and transphosphorylate, independent of the presence of insulin. A more limited deletion which removes part of L2 and most of the CD region activates IR and blunts the action of insulin[18]. Such a deletion removes the physical support for the CR cam region of the partner monomer, thus partly collapsing the cam to permit rapprochement of the TK regions. At the same time the geometry of the insulin binding site in the L2 and CR region would be affected, as well as the insulin-induced change in the relative configuration of the entire L1-CR-L2 regions.

Point Mutations

More subtle alterations of IR are the mutations Phe383Val and Asp919Glu, both of which impair TK action[5,20,21]. Phe383 is midway in the L2 domain[10], which in the model is straddled by the Fn0 linkage to the α—α Cys524 disulphide bond and by the CR cam region of the partner monomer that contacts the Fn2/TM region. The Asp919Glu mutation is at the C-terminal edge of the Fn2 domain of the β subunit (SEQ ID NO:17), which in the model contacts the cam. Size modifications in either of these complementary extracellular contact sites may prevent proper mating of the intracellular TK domains.

Other aspects of the function of IR that can be explained by the arrangement of the domains in the 3D structure include the negative or positive cooperativity of binding of insulin to native or mutant receptors[22-24], the loss of intracellular TK activity from the extracellular Cys647Ser mutation[2], the effect on extracellular binding of insulin by the intracellular TK mutant Met1153Ile[25], the predominantly passive role of the transmembrane region[26-28], and the relative down-stream kinase activity of monomeric and dimeric IR[29].

As three further tests, the model predicts (a) that an antibody linking the two TK domains at their most distal intracellular ends to induce transphosporylation, would increase the high affinity binding of insulin; (b) that a helix breaking amino acid in the transmembrane region would affect TK activation without modifying insulin binding characteristics; and (c) that a genetically engineered shift of the cam bulge via judicious insertion/deletion mutations would invert the response to insulin such that TK activation would be constitutive, but abrogated in the presence of the ligand.

EXAMPLE 10

Method of Identifying Modulators

The three dimensional atomic structure can be readily used as a template for selecting potent modulators. Various computer programs and databases are available for the purpose. A good modulator should at least have excellent steric and electrostatic complementarity to the target, a fair amount of hydrophobic surface buried and sufficient conformational rigidity to minimize entropy loss upon binding. The approach usually comprises several steps.

One must first define a region to target. The ligand binding site of IR or an IR cam can be used, but any place that is essential to the IR activity could become a potential target. Other protein targets include, but are not limited to, structural subdomains, epitopes, and functional domains. Since the fitted quaternary structure has been determined, the spatial and chemical properties of the target region is known.

A compound is then docked onto the target. Many methods can be used to achieve this. Computer databases of three-dimensional structures are available for screening millions of molecular compounds. A negative image of these compounds can be calculated and used to match the shape of the target cavity. The profiles of ionic, hydrophobic, hydrophilic, hydrogen bond donor-acceptor, and lipophilic points of these compounds can be calculated and used to match the shape of the target. Anyone skilled in the art would be able to identify many small molecules or fragment as hits.

One then utilizes linking and extending recognition fragments. Using the hits identified by above procedure, one can incorporate different functional groups or molecules into a single, large molecule. The resulting molecule is likely to be more potent and have higher specificity. It is also possible to try to improve the modulator by adding more atoms or fragments that will interact with the target protein. The originally defined target region can be readily expanded to allow further necessary extension.

A number of promising compounds can be selected through the process. They can then be synthesized and assayed for their agonizing or antagonizing properties.

The present invention has been described in detail and with particular reference to the preferred embodiments; however, it will be understood by one having ordinary skill in the art that changes can be made thereto without departing from the spirit and scope thereof.

All publications, patents and patent applications (including Canadian patent application nos. 2,273,576, 2,292,258 and U.S. patent application Ser. No. 09/461,791) are herein incorporated by reference in their entirety to the same extent as if each individual publication, patent or patent application was specifically and individually indicated to be incorporated by reference in its entirety.

REFERENCES AND NOTES

1. M. Bajaj, M. D. Waterfield, J. Schlessinger, W. R. Taylor, T. Blundell, *Biochim. Biophys. Acta* 916, 220 (1987).
2. A. Ullrich and J. Schlessinger, *Cell* 61, 203 (1990).
3. M. R. White and R. Kahn, *J. Biol. Chem.* 269, 1 (1994).
4. S. R. Hubbard, L. Wei, L. Ellis, W. A. Hendrickson, *Nature* 372, 746 (1994). S. R. Hubbard, *EMBO J.* 16, 5572 (1997).
5. T. P. J. Garrett et al., *Nature* 394, 395 (1998).
5. Bis-(t-Boc)-bovine-insulin (BBI) was prepared as described [R. Geiger, H. H. Schöne, W. Pfaff, *Physiol. Chem.* 352, 1487 (1971)]. 1 mg of BBI and 30 nmole of mono-NHS-Nanogold (Nanoprobes Inc., Stoneybrook, N.Y.) were dissolved in 200 μl of N'N-dimethylacetamide containing 2 μl di-iso-propylethylamine, pH 7.6. After vigorous mixing at room temperature for 60 minutes the mixture was dried in a SpeedVac (Savant Instruments. Inc. Farmingdale, N.Y.). The pellet obtained was dissolved in 20 μl of trifluoroacetic acid, kept at room temperature for 5 minutes, and then dried again. The pellet, resuspended in 120 μl of 1 M acetic acid, was chromatographed twice on a Bio-Gel P-10 column (1.7×25 cm) in 1 M acetic acid. The purified NG-BI was more than 95% pure and had a molecular mass of 19796 Da by matrix-assisted laser desorption/ionization (MALDI) time-of-flight (TOF) mass spectrometry (FIG. 1, inset), consistent with one insulin molecule having been derivatized with one Nanogold cluster.
6. J. Murray-Rust, A. N. McLeod, T. L. Blundell, S. P. Wood, *BioAssay* 14, 325 (1992).
7. Y. Fujita-Yamaguchi, S. Choi, Y. Sakamoto, K. Itakura, *J. Biol. Chem.* 258, 5045 (1983).
8. C. C. Yip, *J. Cell. Biochem.* 48, 19 (1992); L. Schäffer, *Exp. Clin. Endocrinol.* 101, 7 (1993); P. De Meyts et al., *Exp. Clin. Endocrinol.* 101, 17 (1993).
9. P. De Meyts, A. R. Bianco, J. Roth, *J. Biol. Chem.* 251, 1877 (1976).

REFERENCES

1. Luo, R. Z.-T., Beniac D. R., Fernandes, A. B., Yip, C. C. & Ottensmeyer, F. P. Quaternary Structure of the Insulin—Insulin Receptor Complex. *Science* 285, 1077–80 (1999).
2. White, M. F. & Kahn, R. The insulin signaling system. *J. Biol. Chem.* 269, 1–4 (1994).
3. Tulloch, P. A. et al. Single-molecule imaging of human insulin receptor ectodomain and its Fab complexes. *J. Struct. Biol.* 125, 11–18 (1999).
4. Ebina, Y. et al. The human insulin receptor cDNA: the structural basis for hormone-activated transmembrane signalling. *Cell* 40, 747–58 (1985).
5. Taylor, S. I. et al. Mutations in the insulin receptor gene. *Endocrine Rev.* 13, 566–95 (1992).
6. Sparrow, L. G. et al. The disulfide bonds in the C-terminal domains of the human insulin receptor ectodomain. *J. Biol. Chem.* 272, 29460–7 (1997).
7. Kristensen, C., Wiberg, F. C., Schaffer, L. & Andersen, A. S. Expression and characterization of a 70-kDa fragment of the insulin receptor that binds insulin. Minimizing ligand binding domain of the insulin receptor. *J. Biol. Chem.* 273, 17780–6 (1998).
8. Hubbard, S. R., Wei, L., Ellis, L. & Henderson, W. A. Crystal structure of the tyrosine kinase domain of the human insulin receptor. *Nature* 372, 746–54 (1994).

9. Hubbard, S. R. Crystal structure of the activated insulin receptor tyrosine kinase in complex with peptide substrate and ATP analog. *EMBO J.* 16, 5572–81 (1997).
10. Garrett, T. P. J. et al. Crystal structure of the first three domains of the type-I insulin-like growth factor receptor. *Nature* 394, 395–99 (1998).
11. Mulhern, T. D., Brooker, G. W. & Cosgrove, L. A. Third firbronectin-type-III domain in the insulin-family receptors. *Trends Biochem. Sci.* 23, 465–466 (1998).
12. Casasnovas, J. M. Springer, T. A., Liu. J. H., Harrison, S. C. & Wang, J. H. Crystal structure of ICAM-2 reveals a distinctive integrin recognition. *Nature* 387, 312–5 (1997).
13. Copie, V. et al. Solution structure and dynamics of linked cell attachment modules of mouse fibronectin containing the RGD and synergy regions: comparison with the human fibronectin crystal structure. *J. Mol. Biol.* 277, 663–82 (1998).
14. Schaefer, E. M., Erickson, H. P., Federwisch, M., Wollmer, A. & Ellis, L. Structural organization of the human insulin receptor ectodomain. *J. Biol. Chem.* 267, 23393–402 (1992).
15. Schäffer, L. A Model for insulin binding to the insulin receptor. *Eur. J. Biochem.* 221, 1127–32 (1994).
16. Yip, C. C. The insulind-binding domain of insulin receptor is encoded by exon 2 and exon 3. *J. Cell. Biochem.* 48, 19–25 (1992).
17. Boni-Schnetzler, M., Scott, W., Waugh, S. M., DiBella, E. & Pilch, P. F. The insulin receptor. Structural basis for high affinity ligand binding. *J. Biol. Chem.* 262, 8395–401 (1987).
18. Sung, C. K., Wong, K. Y., Yip, C. C., Hawley, D. M. & Goldfine, I. D. Deletion of residues 485–599 from the human insulin receptor abolishes antireceptor antibody binding and influences tyrosine kinase activation. *Mol. Endocrinol.* 8, 315–24 (1994).
19. Shoelson, S. E., White, M. F. & Kahn, C. R. Tryptic activation of the insulin receptor. Proteolytic truncation of the alpha-subunit releases the beta-subunit from inhibitory control. *J. Biol. Chem.* 263, 4852–60 (1988).
20. Grunberger, G., Zick, Y. & Gorden, P. Defect in phosphorylation of insulin receptors in cells from an insulin-resistant patient with normal insulin binding. *Science* 223, 9324 (1984).
21. Roach, P., Arakaki, R. F., Accili, D. & Taylor, S. I. Extreme insulin resistance associated with decreased tyrosine kinase activity: mutation in the insulin receptor β-subunit. *Clin Res.* 40, 311A (1992).
22. Meyts, P., de. Roth, J., Neville, D. M. Jr., Gavin, J. R. 3d. & Lesniak, M. A. Insulin interactions with its receptors: experimental evidence for negative cooperativity. *Biochem. Biophys. Res. Comm.* 55, 154–61 (1973).
23. Yip, C. C. et al. Localization of the insulin-binding site to the cysteine-rich region of the insulin receptor alpha-subunit. *Biochem. Biophys. Res. Comm.* 157, 321–9 (1988).
24. Bilan, P. J. & Yip, C. C. Unusual insulin binding to cells expressing an insulin receptor mutated at cysteine 524. *Biochem. Biophys. Res. Commun.* 205, 1891–8 (1994).
25. Kahn, R. C. et al. The insulin receptor and its substrate: Molecular determinants of early events in insulin action. *Recent Prog. Hormone Res.* 48, 291–339 (1993).
26. Lee, J. & Pilch, P. F. The insulin receptor: structure, function, and signaling. *Amer. J. Physiol.* 266, C319–34 (1994).
27. Frattali, A. L., Treadway, J. L. & Pessin, J. E. Evidence supporting a passive role for the insulin receptor transmembrane domain in insulin-dependent signal transduction. *J. Biol. Chem.* 266, 9829–34 (1991).
28. Longo, N., Shuster, R. C., Griffin, L. D., Langley, S. D. & Elsas, L. J. Activation of insulin receptor signaling by a single amino acid substitution in the transmembrane domain. *J. Biol. Chem.* 267, 12416–9 (1992).
29. Boni-Schnetzler, M., Rubin, J. B. & Pilch, P. F. Structural requirements for the transmembrane activation of the insulin receptor kinase. *J. Biol. Chem.* 261, 15281–7 (1986).
30. De Meyts, P. et al. Identification of a ligand-binding region of the human insulin receptor encoded by eht second exon of the gene. *Molec Endocrinol.* 4, 409–16 (1990).
31. Marino-Buslje, C., Mizuguchi, K., Siddle, K., & Blundell T. L. A third fibronectin type III domain in the extracellular region of the insulin receptor family. *FEBS Letters* 441, 331–36 (1998).
32. Chiacchia, K. B. Quantitation of the class I disulfides of the insulin receptor. *Biochem. Biophys. Res. Comm.* 176, 1178–82, 1991.
33. Zhang B. & Roth R A. A region of the insulin receptor important for ligand binding (residues 450–601) is recognized by patients' autoimmune antibodies and inhibitory monoclonal antibodies. *Proc. Natl. Acad. Sci.* 88, 9858–62, 1991
34. Murray-Rust, J., NcLeod, A. N., Blundell, T. L. & Wood. S. P. Structure and evolution of insulins: Implications for recepto binding. BioEssays 14, 325–31, 1992.
35. Schwartz G P. Burke G T. Katsoyannis P G. A highly potent insulin: des-(B26-B30)-[AspB10, TyrB25-NH2] insulin (human). Proc. Natl. Acad. Sci. USA 86,458–61, 1989
36. Williams, F. P. Mynarcik, D. C., Yu, G. Q. & Whittaker, J. Mapping of an $NH_2$-terminal ligand binding site of the insulin receptor by alanine scanning matagenesis. J. Biol. Chem. 270, 3012–16, 1995
37. Rigby, A. C., Barber, K. R. Shaw, G. S. & Grant, C. W. Transmembrane region of the epidermal growth factor recepto: Behaviour and interactions via $^2H$ NMR. Biochemistry 35, 12591–601, 1996.

We claim:

1. A method of determining whether a compound modulates insulin receptor activity, comprising comparing all or part of the structure of the compound to all or part of the fitted quaternary structure of an insulin receptor to determine how the compound interacts with the insulin receptor, the comparing step comprising:
    providing a computer program on a processor, the computer program including structural coordinates defining a ligand binding site conformation including at least one residue from monomer A in Table 1 and at least one residue from monomer B in Table 1, wherein the ligand binding site is defined by the approximate amino acid intersidechain distances listed in Table 1;
    said program displaying all or part of the fitted quaternary structure of the insulin receptor including the ligand binding site;
    comparing the structural coordinates of the compound to the structural coordinates of the ligand binding site and determining whether the compound fits spatially into the ligand binding site;
    wherein if the compound fits spatially into the ligand binding site, next determining whether the compound modulates the insulin receptor by determining if the compound agonizes the insulin receptor activity by performing an insulin receptor activity assay.

2. The method of claim 1, wherein the fitted quaternary structure of the insulin receptor comprises substantially the entire fitted quaternary structure of insulin receptor.

3. The method of claim 1, wherein the insulin receptor is bound to insulin.

4. A method of determining whether a compound modulates insulin receptor activity, comprising comparing all or part of the structure of the compound to all or part of the fitted quaternary structure of an insulin receptor to determine how the compound interacts with the insulin receptor, the comparing step comprising:
    providing a computer program on a processor, the computer program including structural coordinates defining a ligand binding site conformation including at least one residue from monomer A in Table 1 and at least one residue from monomer B in Table 1, wherein the ligand binding site is defined by the approximate amino acid intersidechain distances listed in Table 1;
    said program displaying all or part of the fitted quaternary structure of the insulin receptor including the ligand binding site;
    comparing the structural coordinates of the compound to the structural coordinates of the ligand binding site and determining whether the compound fits spatially into the ligand binding site;
    wherein if the compound fits spatially into the ligand binding site, next determining whether the compound modulates the insulin receptor activity by determining whether the compound antagonizes the insulin receptor activity by performing an insulin receptor activity assay.

5. The method of claim 4, wherein the insulin receptor is bound to insulin.

6. A method of determining whether a compound modulates insulin receptor activity, comprising comparing all or part of the structure of the compound to all or part of the fitted quaternary structure of an insulin receptor to determine how the compound interacts with the insulin receptor, the comparing step comprising:
    providing a computer program on a processor, the computer program including structural coordinates including at least one first residue from between amino acids 250 to 280 of FIG. 12 and at least one second residue from the L1 surface in Table 2;
    said program displaying all or part of the fitted quaternary structure of the insulin receptor including the first and second residues;
    comparing the structural coordinates of the compound to the structural coordinates of the first and second residues and determining whether the compound interacts with said first and second residues;
    wherein if the compound fits spatially between said first and second residues, next determining whether the compound modulates the insulin receptor activity by determining whether the compound agonizes the insulin receptor activity by performing an insulin receptor activity assay.

7. The method of claim 6, wherein the insulin receptor is bound to insulin.

8. The method of claim 6, wherein the at least one first residue between amino acids 250 to 280 of FIG. 12 comprises at least one residue selected from the group consisting of Lys265, Lys267, Asn268, Arg270, Arg271 and Gln272.

9. A method of determining whether a compound modulates insulin receptor activity, comprising comparing all or part of the structure of the compound to all or part of the fitted quaternary structure of an insulin receptor to determine how the compound interacts with the insulin receptor, the comparing step comprising:
    providing a computer program on a processor, the computer program including structural coordinates including at least one first residue from residue between amino acids 250 to 280 of FIG. 12 and at least one second residue from the L1 surface in Table 2;
    said program displaying all or part of the fitted quaternary structure of the insulin receptor including the first and second residues;
    comparing the structural coordinates of the compound to the structural coordinates of the first and second residues and determining whether the compound interacts with said first and second residues;
    wherein if the compound fits spatially between said first and second residues, next determining whether the compound modulates the insulin receptor activity by determining whether the compound agonizes the insulin receptor activity by performing an insulin receptor activity assay.

10. The method of claim 9, wherein the insulin receptor is bound to insulin.

11. The method of claim 9, wherein the at least one first residue between amino acids 250 to 280 of FIG. 12 comprises at least one residue selected from the group consisting of Lys265, Lys267, Asn268, Arg270, Arg271 and Gln272.

* * * * *